(12) United States Patent
Fatatis et al.

(10) Patent No.: US 10,517,933 B2
(45) Date of Patent: Dec. 31, 2019

(54) METHOD OF TREATING ANDROGEN RECEPTOR NEGATIVE PROSTATE TUMORS AND THEIR METASTASES

(71) Applicant: DREXEL UNIVERSITY, Philadelphia, PA (US)

(72) Inventors: Alessandro Fatatis, Penn Valley, PA (US); Danielle Jernigan, Ardmore, PA (US); Kristina Susan Shahriari, Philadelphia, PA (US); Fei Shen, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 15/566,031

(22) PCT Filed: May 11, 2016

(86) PCT No.: PCT/US2016/031820
§ 371 (c)(1),
(2) Date: Oct. 12, 2017

(87) PCT Pub. No.: WO2016/183176
PCT Pub. Date: Nov. 17, 2016

(65) Prior Publication Data
US 2018/0110835 A1 Apr. 26, 2018

Related U.S. Application Data

(60) Provisional application No. 62/160,114, filed on May 12, 2015.

(51) Int. Cl.
| | |
|---|---|
| A61K 38/20 | (2006.01) |
| A61K 45/06 | (2006.01) |
| A61K 31/522 | (2006.01) |
| A61K 31/573 | (2006.01) |
| A61K 31/713 | (2006.01) |
| A61K 38/14 | (2006.01) |
| A61K 38/17 | (2006.01) |
| A61K 38/21 | (2006.01) |
| A61K 38/50 | (2006.01) |
| A61P 35/04 | (2006.01) |
| A61P 35/00 | (2006.01) |
| G01N 33/574 | (2006.01) |

(52) U.S. Cl.
CPC ............ *A61K 38/20* (2013.01); *A61K 31/522* (2013.01); *A61K 31/573* (2013.01); *A61K 31/713* (2013.01); *A61K 38/14* (2013.01); *A61K 38/1793* (2013.01); *A61K 38/217* (2013.01); *A61K 38/50* (2013.01); *A61K 45/06* (2013.01); *A61P 35/00* (2018.01); *A61P 35/04* (2018.01); *G01N 33/57434* (2013.01); *G01N 2333/723* (2013.01)

(58) Field of Classification Search
None
See application file for complete search history.

(56) References Cited

U.S. PATENT DOCUMENTS

| 6,368,598 B1 | 4/2002 | D'Amico et al. |
| 8,742,141 B2 | 6/2014 | Bergan et al. |
| 2014/0349935 A1 | 11/2014 | Persson |
| 2015/0023920 A1 | 1/2015 | Fatatis et al. |

FOREIGN PATENT DOCUMENTS

| WO | 03094844 A2 | 11/2003 | |
| WO | WO2013148202 | * 10/2013 | ............... C12Q 1/00 |
| WO | 2014060477 A1 | 4/2014 | |
| WO | WO2013/148202 | * 10/2014 | ............... C12Q 1/00 |

OTHER PUBLICATIONS

International Search Report and Written Opinion for PCT International Application No. PCT/US2016/031820 dated Aug. 18, 2016.
Extended European Search Report for European Patent Application No. 16793431.4 dated Dec. 12, 2018.
Owyang, et al., XOMA 052, a potent, high-affinity monoclonal antibody for the treatment of IL-1β-mediated diseases, MAbs. 3(1) ,Jan.-Feb. 2011 ,49-60.

* cited by examiner

*Primary Examiner* — Elly-Garald Stoica
(74) *Attorney, Agent, or Firm* — Saul Ewing Arnstein & Lehr LLP; Kathryn Doyle; Domingos J. Silva

(57) ABSTRACT

The invention includes a method of preventing or treating metastasis in a subject diagnosed with prostate cancer. In certain embodiments, the metastasis comprises bone cancer. In other embodiments, the subject suffers from castration-resistant prostate cancer.

6 Claims, 26 Drawing Sheets

Specification includes a Sequence Listing.

| SAMPLE | SYNAPTOPHYSIN | CHROMOGRANIN A |
|---|---|---|
| MOUSE NEURONAL CULTURE | POSITIVE | POSITIVE |
| BONE MET #1 [AR +] | NEGATIVE | NEGATIVE |
| BONE MET #2 [AR+] | NEGATIVE | NEGATIVE |
| BONE MET #1 [AR –] | NEGATIVE | NEGATIVE |
| BONE MET #1 [AR –] | NEGATIVE | NEGATIVE |
| LUNG [AR –] | POSITIVE | POSITIVE | ns. Metastatic disease is primarily, but not uniquely, associated with malignant tumor cells and infections.
METHOD OF TREATING ANDROGEN RECEPTOR NEGATIVE PROSTATE TUMORS AND THEIR METASTASES

CROSS-REFERENCE TO RELATED APPLICATIONS

This application is a 35 U.S.C. § 371 national phase application from, and claims priority to, International Application No. PCT/US2016/031820, filed May 11, 2016, and published under PCT Article 21(2) in English, which claims priority to U.S. Provisional Application No. 62/160,114, filed May 12, 2015, all of which applications are incorporated herein by reference in their entireties.

BACKGROUND OF THE INVENTION

Metastasis or metastatic disease is the spread of a disease from one organ or part to another non-adjacent organ or part. Metastatic disease is primarily, but not uniquely, associated with malignant tumor cells and infections.

Cancer occurs after a single cell in a tissue is genetically damaged in ways that result in the formation of a putative cancer stem cell possessing a malignant phenotype. These cancer stem cells are able to undergo uncontrolled abnormal mitosis, which serves to increase the total number of cancer cells at that location. When the area of cancer cells at the originating site become clinically detectable, it is called primary tumor. Some cancer cells also acquire the ability to penetrate and infiltrate surrounding normal tissues in the local area, forming a new tumor. The newly formed tumor in the adjacent site within the tissue is called a local metastasis.

Some cancer cells acquire the ability to penetrate the walls of lymphatic and/or blood vessels, after which they are able to circulate through the bloodstream (circulating tumor cells) to other sites and tissues in the body. This process is known (respectively) as lymphatic or hematogenous spread. After the tumor cells come to rest at another site, they re-penetrate through the vessel or walls (extravasation), continue to multiply, and eventually another clinically detectable tumor is formed. This new tumor is known as a metastatic (or secondary) tumor. Metastasis is one of the hallmarks of malignancy. Most tumors and other neoplasms can metastasize, although in varying degrees (e.g., basal cell carcinoma rarely metastasizes).

Metastatic tumors are very common in the late stages of cancer. The most common places for the metastases to occur are the lungs, liver, brain, and the bones. There is also a propensity for certain tumors to seed in particular organs. For example, prostate cancer and breast cancer usually metastasizes to the bones. Colon cancer has a tendency to metastasize to the liver. Stomach cancer often metastasizes to the ovaries in women. Studies have suggested that these tissue-selective metastases processes are due to specific anatomic and mechanical routes. In particular, a cancer cell may colonize other organs and progress into macroscopic lesions only if its genotypic and phenotypic features are somehow compatible with the local microenvironment. Thus, the identification of the molecular determinants underpinning cancer cells colonization of secondary organs may reveal novel therapeutic targets to effectively counteract metastatic disease.

Prostate cancer develops in the prostate, a gland in the male reproductive system, and often affects men over the age of fifty. Prostate cancer is most common in the developed world, with increasing rates in the developing world. Globally, it is the sixth leading cause of cancer-related death in men, but it is the first in the United Kingdom and the second in the U.S. However, many men with prostate cancer never develop symptoms, do not undergo therapy, and eventually die of other unrelated causes. Many factors, including genetics and diet, have been implicated in the development of prostate cancer.

Most prostate cancers are slow growing; but there are cases of aggressive prostate cancers. The cancer cells may metastasize from the prostate to other parts of the body, particularly the bones and lymph nodes. Prostate cancer may cause pain, difficulty in urinating, problems during sexual intercourse, or erectile dysfunction. Chemotherapy has been widely used for prostate cancer treatments. Recent studies have focused on chemotherapy-induced apoptosis of tumor cells to inhibit tumor cell growth and promote cell death.

Two important molecular targets for prostate cancer treatment include prostate tissue secreted growth factors, such as transforming growth factor type-P (TGF-P) and prostate-specific antigen (PSA). TGF-P regulates cell growth, differentiation, and development of a variety of functions. PSA, a chymotrypsin-like serine protease known as gamma-seminoprotein or human glandular kallikrein-related peptidase-3 (KLK3), is secreted from epithelial prostate tissue, where it is highly localized. PSA screening has been used to identify individuals with prostate cancer. However, PSA is an indicator of not only prostate cancer, but also prostatitis or benign prostatic hyperplasia. In fact, only 30% with high PSA have prostate cancer diagnosed after biopsy. Although therapies targeting the androgen receptor, an upstream regulator of PSA, have been effective in treating prostate cancer, the disease state sometimes progresses and results in castrate-resistant prostate cancer (CRPC). The androgen receptor (AR) is widely thought to play a vital role also in the disseminated CRPC, which affects primarily the skeleton.

Interleukin-1 beta (IL1β; SEQ ID NO: 1 for IL-1β precursor and SEQ ID NO:2 for cleaved mature IL-1β), also known as catabolin, is a cytokine protein, which in humans is encoded by the IL1B gene. IL1β is a member of the interleukin 1 cytokine family and produced by activated macrophages as a pro-protein, which is proteolytically processed to its active form by caspase 1 (CASP1/ICE). This cytokine is an important mediator of the inflammatory response, and involved in cellular activities including cell proliferation, differentiation, and apoptosis. Studies associate the gene with susceptibility to schizophrenia.

There is a need in the art to develop novel methods of treatment that avoid, delay or minimize the development of metastatic tumors in a subject, especially in the context of metastatic bone cancer associated with primary prostate cancers. The present invention fulfills this need.

BRIEF SUMMARY OF THE INVENTION

The invention provides a method of killing, and/or preventing or reducing the growth of, a prostate cancer cell that does not express androgen receptor [AR(−) PC cell]. The invention further provides a method of treating or preventing metastasis of a AR(−) PC cell in a subject. The invention further provides a method of treating or preventing bone metastasis of a prostate cancer cell that expresses androgen receptor and does not express IL1β [AR(+)/IL1β(−) PC cell] in a subject. The invention further provides a method of recommending anti-metastasis therapeutic treatment for a subject suffering from prostate cancer. The invention further provides a method of identifying a prostate cancer patient who will benefit from an anti-metastasis therapeutic treatment comprising an IL1β-depleting agent. The invention further provides a method of determining if a prostate cancer patient is benefiting from an anti-metastasis therapeutic treatment comprising an IL1β-depleting agent. The invention further provides a kit comprising an IL1β-depleting agent, and an instructional material for use thereof.

In certain embodiments, the method comprises contacting the AR(−) PC cell with an effective amount of an IL1β-depleting agent, whereby the cell is killed and/or growth of the cell is prevented or reduced.

In certain embodiments, the method comprises administering to the subject a therapeutically effective amount of an IL1β-depleting agent, whereby metastasis of the AR(−) PC cell in the subject is treated or prevented.

In certain embodiments, the method comprises administering to the subject a therapeutically effective amount of an IL1β-depleting agent, whereby bone metastasis of the cell in the subject is treated or prevented.

In certain embodiments, the method comprises determining whether a biological sample from the subject comprises a AR(+)/IL1β(−) PC cell or a AR(−) PC cell, wherein, if the biological sample from the subject comprises a AR(+)/IL1β(−) PC cell or a AR(−) PC cell, the subject is instructed to undergo anti-metastatic therapeutic treatment using a therapeutically effective amount of an IL1β-depleting agent.

In certain embodiments, the method comprises assessing in a biological sample of the patient the level of at least one marker selected from the group consisting of: PCADM-1, antibody that binds to PCADM-1, and polynucleotide encoding PCADM-1. In other embodiments, the method comprises comparing the level of the at least one marker in the patient's biological sample with the level of the at least one marker in a biological sample obtained from a like mammal not afflicted with metastatic prostate cancer. In yet other embodiments, a higher level of the at least one marker in the patient's biological sample as compared to the level of the at least one marker in the like mammal's biological sample indicates that the patient will benefit from anti-metastatic therapeutic treatment comprising an IL1β-depleting agent.

In certain embodiments, the method comprises assessing, in at least first and second biological samples of the patient, the level of at least one marker selected from the group consisting of: PCADM-1, antibody that binds to PCADM-1, and polynucleotide encoding PCADM-1. In other embodiments, the first sample is obtained before the patient is administered an IL1β-depleting agent, and the second sample is obtained after the patient is administered an IL1β-depleting agent, or the first sample and second samples are obtained after the patient is administered an IL1β-depleting agent, the second sample being obtained at a later time point of the treatment. In yet other embodiments, the method comprises comparing the levels of the at least one marker in the patient's at least first and second biological samples. In yet other embodiments, a lower level of the at least one marker in the patient's second biological sample as compared to the level of the at least one marker in the patient's first biological sample indicates that the patient is responding to the anti-metastatic therapeutic treatment comprising an IL1β-depleting agent. In yet other embodiments, an equal or higher level of the at least one marker in the patient's second biological sample as compared to the level of the at least one marker in the patient's first biological sample indicates that the patient is not responding to the anti-metastatic therapeutic treatment comprising an IL1β-depleting agent.

In certain embodiments, the cell is in vitro or ex vivo. In other embodiments, the cell is part of a solid tumor within a subject. In yet other embodiments, the solid tumor comprises a prostate tumor. In yet other embodiments, the solid tumor comprises a bone metastasis. In yet other embodiments, the metastasis comprises bone metastasis. In yet other embodiments, the subject suffers from castration-resistant prostate cancer.

In certain embodiments, the IL1β-depleting agent is selected from the group consisting of anakinra, XOMA-052, AMG-108, canakinumab, rilonacept, K-832, CYT-013-IL1bQb, LY-2189102, dexamethasone, interferon-gamma, pentoxifylline, IL1β antibody, siRNA, ribozyme, antisense, aptamer, peptidomimetic, small molecule, and any combinations thereof.

In certain embodiments, the IL1β antibody comprises an antibody selected from the group comprising a polyclonal antibody, monoclonal antibody, humanized antibody, synthetic antibody, heavy chain antibody, human antibody, biologically active fragment of an antibody, and any combinations thereof.

In certain embodiments, the cell is mammalian. In other embodiments, the cell is human.

In certain embodiments, the subject is further administered at least one additional compound selected from the group consisting of a chemotherapeutic agent and anti-cell proliferation agent. In other embodiments, the chemotherapeutic agent comprises at least one additional compound selected from the group consisting of an alkylating agent, nitrosourea, antimetabolite, antitumor antibiotic, plant alkyloid, taxane, hormonal agent, bleomycin, hydroxyurea. L-asparaginase, and procarbazine. In yet other embodiments, the anti-cell proliferation agent comprises at least one additional compound selected from the group consisting of a granzyme, Bcl-2 family member, cytochrome C, and caspase. In yet other embodiments, the IL1β-depleting agent and the at least one additional compound are co-administered to the subject. In yet other embodiments, the IL1β-depleting agent and the at least one additional compound are co-formulated and co-administered to the subject.

In certain embodiments, the IL1β-depleting agent is administered to the subject by an administration route selected from the group consisting of inhalational, oral, rectal, vaginal, parenteral, topical, transdermal, pulmonary, intranasal, buccal, ophthalmic, intrathecal, and any combinations thereof. In other embodiments, the subject is a mammal. In yet other embodiments, the mammal is a human.

In certain embodiments, the subject is instructed not to undergo androgen-deprivation therapy (ADT). In other embodiments, the antibody binds specifically to PCADM-1 and does not cross-react non-specifically with human S2 ribosomal protein. In yet other embodiments, the method further comprises instructing the patient to undergo anti-metastasis therapeutic treatment comprising an IL1β-depleting agent. In yet other embodiments, the method further comprises administering to the patient anti-metastasis therapeutic treatment comprising an IL1β-depleting agent. In yet other embodiments, the patient is responding to the anti-metastatic therapeutic treatment comprising an IL1β-depleting agent, and wherein the subject is instructed to maintain the therapeutic treatment comprising an IL1β-depleting agent treatment. In yet other embodiments, the patient is not responding to the anti-metastatic therapeutic treatment comprising an IL1β-depleting agent, and wherein the subject is instructed to discontinue the therapeutic treatment comprising an IL1β-depleting agent treatment.

In certain embodiments, the instructional material comprises instructions for preventing or treating preventing metastasis of a AR(−) PC cell or AR(+)/IL1β(−) PC cell. In other embodiments, the kit further comprises at least one additional compound selected from the group consisting of a chemotherapeutic agent and an anti-cell proliferation agent. In yet other embodiments, the subject suffers from CRPC.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 3C is a set of images that illustrates effects of knocking out IL1R on bone metastatic lesions. FIG. 3D is a bar graph that illustrates the number of mice that develop (or not) bone metastatic lesions, as a function of their IL1R status. FIG. 3E is a bar graph that illustrates the tumor burden of the mouse as a function of their IL1R status.

FIG. 5L demonstrates that a range of PCa cell lines all have the receptor for paracrine IL-1β. FIG. 5M demonstrates differing signal transduction among two Ar+ PCa cell lines which benefitted equally from PC3-ML cells when colonizing a bone, indicating that paracrine stimulation of IL-1R is unlikely to be primarily responsible for metastatic cell cooperation. FIG. 5N demonstrates that human bone Mesenchymal Stem Cells (hMSCs) when exposed to IL-1β exhibit rapid and sustained signaling response, indicating susceptibility to IL-1β.

FIG. 5Q depicts a Western blot showing high IL-1 expression in these cells. FIG. 5R is a graph reporting is an image depicting mixed tumors on the femur and tibia of a mouse after a single inoculation with the highly expressing cells

DETAILED DESCRIPTION OF THE INVENTION

Figure 1A:
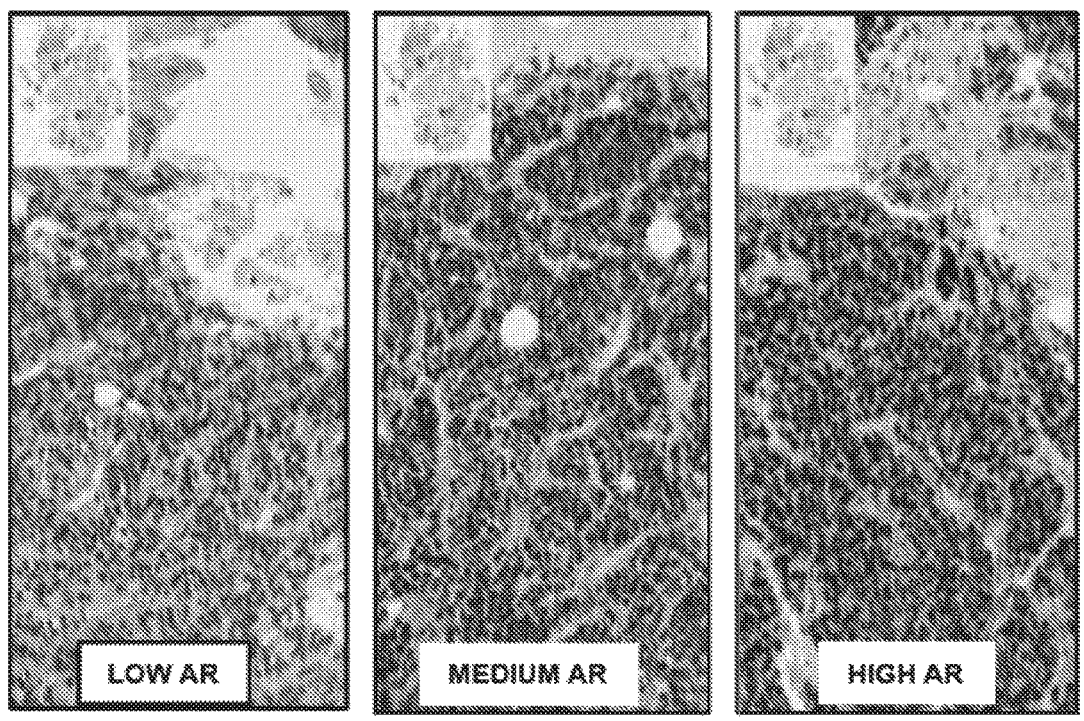
FIG. 1A is a set of images illustrating expression of androgen receptor (AR) in primary tumors and metastatic lesions at the skeletal level.

The present invention relates in part to the unexpected discovery that IL1β deleting therapy is effective in treating or preventing metastasis of cells derived from prostate cancer cells that do not express androgen receptor (AR) (indicated herein as AR(−) PC cells).

As demonstrated herein, human specimens were examined by laser capture microdissection (LCM) and qRT-PCR. The analysis indicated that about 30% of PCa cells in skeletal metastases lack AR and express high levels of Interleukin-1β (IL1β). In contrast, AR-expressing cancer cells are negative for this cytokine. An animal model was used to show that AR(−)/IL1β(+) cancer cells affect the surrounding bone stroma, promoting the development of cancer-associated fibroblasts (CAF) and the expression of cyclooxygenase 2 (COX-2). Notably, transgenic mice knock-out for the IL1β receptor (IL1R) were much less prone to skeletal colonization by AR(−)/IL1β(+) cancer cells, similarly to animals treated with the IL1R antagonist anakinra. These results indicates that tumor-derived IL1β co-opts the bone stroma to establish a metastasis-permissive microenvironment. Remarkably, this metastatic niche also supports AR-expressing, IL1β-lacking PCa cells, which are unable to independently metastasize to the skeleton in the animal model. In certain embodiments, the cancer cell-cooperation identified herein is instrumental for the skeletal colonization in PCa and reveals novel molecular targets for therapeutic strategies aimed to prevent the contribution of AR(−)/IL1β(+) to the establishment and progression of metastatic CRPC.

In one aspect, the invention provides novel methods of identifying those patients that will benefit from treatment with the compositions contemplated within the invention. Prostate Cancer Antigen Diagnostic Marker 1 ("PCADM-1"; SEQ ID NO:3) is highly expressed by AR(−)/IL1β(+) prostate cancer cells. Further, the PSA gene (Prostate Specific Antigen gene) is directly under the transcriptional control of the AR. It thus follows that prostate cancer cells lacking AR cannot express PSA but are positive to PCADM-1.

During the late stages of advanced prostate cancer, metastatic lesions are detected not only at the skeletal level, but also in soft-tissue organs such as lungs and liver. As shown herein, the cancer cells generating these lesions are predominantly AR(−). As a consequence, in these late-stage patients disease progression cannot be reliably monitored by measuring only PSA levels—such information would be limited to the AR(+) component of the metastatic tumor fraction and would wholly neglect the contribution of AR(−) tumor cells. In contrast, assessing the levels of PCADM-1 in plasma or urine, alone, or in combination with PSA would allow physicians to monitor the extent of both AR(+) and AR(−) tumor components during disease progression. Thus, measuring PCADM-1 levels in biological samples of a patient suffering from prostate cancer allows for the stratification of those patients that can benefit more from these therapeutics as compared to patients with a predominant AR(+) tumor fraction.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "ADT" refers to androgen-deprivation therapy.

As used herein, the term "alphaMSA" refers to alpha smooth muscle actin.

The term "antibody" as used herein refers to an immunoglobulin molecule able to specifically bind to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies (Harlow et al., 1998, Using Antibodies: A Laboratory Manual, Cold Spring Harbor Laboratory Press, NY, Harlow et al. 1989, Antibodies: A Laboratory Manual, Cold Spring Harbor, N.Y.; Houston et al. 1988, Proc. Natl. Acad. Sci. USA 85:5879-5883; Bird et al., 1988, Science 242:423-426).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized, or can be derived from a biological sample. Such a biological sample can be obtained from, but not limited to, a tissue (such as prostate or bone marrow), tumor (such as prostate), cell, or biological fluid (such as blood, urine, sputum, peritonial cavity fluid, perineal cavity fluid, pleural cavity fluid, semen, prostatic fluid, and stool).

By the term "applicator." as the term is used herein, is meant any device including, but not limited to, a hypodermic syringe, a pipette, and the like, for administering the compounds and compositions of the invention.

As used herein, "aptamer" refers to a small molecule that can bind specifically to another molecule. Aptamers are typically either polynucleotide- or peptide-based molecules.

A polynucleotidal aptamer is a DNA or RNA molecule, usually comprising several strands of nucleic acids, that adopts highly specific three-dimensional conformation designed to have appropriate binding affinities and specificities towards specific target molecules, such as peptides, proteins, drugs, vitamins, among other organic and inorganic molecules. Such polynucleotidal aptamers can be selected from a vast population of random sequences through the use of systematic evolution of ligands by exponential enrichment. A peptide aptamer is typically a loop of about 10 to about 20 amino acids attached to a protein scaffold that bind to specific ligands. Peptide aptamers may be identified and isolated from combinatorial libraries, using methods such as the yeast two-hybrid system.

As used herein, the term "AR" refers to androgen receptor.

As used herein, the term "CAF" refers to cancer-associated fibroblast.

As used herein, the term "cancer" is defined as disease characterized by the rapid and uncontrolled growth of aberrant cells. Cancer cells can spread locally or through the bloodstream and lymphatic system to other parts of the body. Examples of various cancers include but are not limited to, bone cancer, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

As used herein, the term "COX-2" refers to cyclooxygenase 2.

As used herein, the term "CRPC" refers to castrate-resistant prostate cancer.

As used herein, a "disease" is a state of health of an animal wherein the animal cannot maintain homeostasis, and wherein if the disease is not ameliorated then the animal's health continues to deteriorate.

As used herein, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "DTC" refers to a disseminated tumor cell.

As used herein, the terms "effective amount" or "therapeutically effective amount" or "pharmaceutically effective amount" of a compound are used interchangeably to refer to the amount of the compound that is sufficient to provide a beneficial effect to the subject to which the compound is administered. "Treating," as used herein, means reducing the frequency with which symptoms are experienced by a patient or subject, or administering an agent or compound to reduce the severity with which symptoms are experienced by a patient or subject. An appropriate therapeutic amount in any individual case may be determined by one of ordinary skill in the art using routine experimentation.

As used herein "endogenous" refers to any material from or produced inside an organism, cell, tissue, or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly five amino acids and/or sugars in size. One skilled in the art understands that generally the overall three-dimensional structure, rather than the specific linear sequence of the molecule, is the main criterion of antigenic specificity and therefore distinguishes one epitope from another.

As used herein, the term "exogenous" refers to any material introduced from or produced outside an organism, cell, tissue or system.

As used herein, the term "heavy chain antibody" or "heavy chain antibodies" comprises immunoglobulin molecules derived from camelid species, either by immunization with an antigen and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of $V_H$ (variable heavy chain immunoglobulin) genes from an animal.

As used herein, the term "IL1β" or "IL-1β" refers to interleukin 1β.

As used herein, the term "IL1β-depleting agent" refers to an agent that reduces the expression, production and/or circulating concentration of IL1β in a subject treated with such agent. In certain embodiments, the agent is an antibody that binds to and neutralizes IL1β. In other embodiments, the agent is a chemical compound that inhibits formation of IL1β. In yet other embodiments, the agent reduces the expression or production of IL1β in the subject. Agents that reduce the expression, production and/or circulating concentration of IL1β by any physiological mechanism are considered useful within the methods of the invention. In certain embodiments, the IL1β-depleting agent is selected from the group consisting of anakinra, XOMA-052, AMG-108, canakinumab, rilonacept, K-832, CYT-013-IL1bQb, LY-2189102, dexamethasone, interferon-gamma, pentoxifylline, and any combinations thereof.

The terms "inhibit" and "antagonize", as used herein, mean to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

As used herein, the term "LCM" refers to laser capture microdissection.

As used herein, the term "MSC" refers to mesenchymal stem cell.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

As used herein, the term "non-cancer control sample" as relating to a subject's tissue refers to a sample from the same tissue type, obtained from the patient, wherein the sample is known or found not to be afflicted with cancer. For example, a non-cancer control sample for a subject's lung tissue refers to a lung tissue sample obtained from the subject, wherein the sample is known or found not to be afflicted with cancer. "Non-cancer control sample" for a subject's tissue also refers to a reference sample from the same tissue type, obtained from another subject, wherein the sample is known or found not to be afflicted with cancer. "Non-cancer control sample" for a subject's tissue also refers to a standardized set of data (such as, but not limited to, identity and levels of gene expression, protein levels, pathways activated or deactivated and so forth), originally obtained from a sample of the same tissue type and thought or considered to be a representative depiction of the non-cancer status of that tissue.

As used herein, the term "PCa" refers to prostate cancer.

As used herein, the term "PCADM-1" refers to Prostate Cancer Antigen Diagnostic Marker 1. PCADM-1 and antibodies directed to same are described in U.S. Pat. Nos. 7,790,861; 7,939,274; and 8,206,899, all of which are incorporated herein in their entireties by reference.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth: malt; gelatin; talc: excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar: buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent: sweetening agent; flavoring agent; perfuming agent: preservative: antioxidant; plasticizer; gelling agent; thickener; hardener; setting agent; suspending agent; surfactant; humectant; carrier; stabilizer: and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

As used herein, the term "pharmaceutical composition" refers to a mixture of at least one compound useful within the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound include, but are not limited to, intravenous, oral, aerosol, parenteral, ophthalmic, pulmonary and topical administration.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer. The term "protein" typically refers to large polypeptides. The term "peptide" typically refers to short polypeptides. Conventional notation is used herein to portray polypeptide sequences: the left-hand end of a polypeptide sequence is the amino-terminus: the right-hand end of a polypeptide sequence is the carboxyl-terminus. As used herein, a "peptidomimetic" is a compound containing non-peptidic structural elements that is capable of mimicking the biological action of a parent peptide. A peptidomimetic may or may not comprise peptide bonds.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease. Disease and disorder are used interchangeably herein.

By the term "specifically bind" or "specifically binds," as used herein, is meant that a first molecule (e.g., an antibody) preferentially binds to a second molecule (e.g., a particular antigenic epitope), but does not necessarily bind only to that second molecule.

A "subject" or "individual" or "patient," as used therein, can be a human or non-human mammal. Non-human mammals include, for example, livestock and pets, such as ovine, bovine, porcine, canine, feline and murine mammals. In certain embodiments, the subject is human.

By the term "synthetic antibody" as used herein, is meant an antibody generated using recombinant DNA technology, such as, for example, an antibody expressed by a bacteriophage as described herein. The term should also be construed to mean an antibody generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "TAF" refers to tumor associated fibroblast.

As used herein, the term "treatment" or "treating" is defined as the application or administration of a therapeutic agent. i.e., a compound useful within the invention (alone or in combination with another pharmaceutical agent), to a subject, or application or administration of a therapeutic agent to an isolated tissue or cell line from a subject (e.g., for diagnosis or ex vivo applications), who has cancer, a symptom of cancer or the potential to develop cancer, with the purpose to cure, heal, alleviate, relieve, alter, remedy, ameliorate, improve or affect cancer, the symptoms of cancer or the potential to develop cancer. Such treatments may be specifically tailored or modified, based on knowledge obtained from the field of pharmacogenomics.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compositions

In certain embodiments, a composition useful within the methods of the invention comprises at least one IL1β-depleting agent. In other embodiments, a composition useful within the methods of the invention consists essentially of at least one IL1β-depleting agent. In yet other embodiments, a composition useful within the methods of the invention consists of at least one IL1β-depleting agent.

The agent contemplated within the invention reduces the expression, production and/or circulating concentration of IL1β in a subject. In certain embodiments, the agent is an antibody that binds to and neutralizes IL1β. In other embodiments, the agent is a chemical compound that inhibits formation of IL1β. In yet other embodiments, the agent reduces the expression or production of IL1β in the subject. In yet other embodiments, the agent is selected from the group consisting of anakinra, XOMA-052, AMG-108, canakinumab, rilonacept, K-832, CYT-013-IL1bQb, LY-2189102, dexamethasone, interferon-gamma, pentoxifylline, and any combinations thereof. Agents that reduce the expression, production and/or circulating concentration of IL1β by any physiological mechanism are considered useful within the methods of the invention.

Non-limiting examples of IL1β-depleting agents contemplated within the methods of the invention are:

Dexamethasone (8S,9R,10S,11S,13S,14S,16R,17R)-9-Fluoro-11,17-dihydroxy-17-(2-hydroxyacetyl)-10,13,16-trimethyl-6,7,8,9,10,11,12,13,14,15,16,17-dodecahydro-3H-cyclopenta[a]phenanthren-3-one) or a salt thereof: a known inhibitor of IL1β production (Kern et al., 1998, J. Clin. Invest. 81:237-244);

Canakinumab (also known as Ilaris®, Novartis; previously ACZ885: Dhimolea, 2010, Mabs 2(1):3-13) is a human monoclonal antibody targeted at interleukin-1 beta. It has no cross-reactivity with other members of the interleukin-1 family, including interleukin-1 alpha (Lachmann et al., 2009, New Engl. J. Med. 360(23):2416-25). Canakinumab was approved for the treatment of cryopyrin-associated periodic syndromes (CAPS) by the FDA on June 2009 and the European Medicines Agency in October 2009. Canakinumab is also in clinical trials as a possible treatment for chronic obstructive pulmonary disease (Yasothan & Kar, 2008, Nat. Rev. Drug Discov. 7(4):285).

Rilonacept (also known as IL1 Trap or Arcalyst®, Regeneron): an interleukin 1 inhibitor (Drug News Perspect. 21(4): 232). Rilonacept is a dimeric fusion protein consisting of the extracellular domain of human interleukin-1 receptor and the FC domain of human IgG1 that binds and neutralizes IL1. Rilonacept is used for the treatment of cryopyrin-associated periodic syndromes (CAPS).

AMG-108: a fully human monoclonal antibody that targets inhibition of the action of interleukin-1 (Cardiel et al., Arthritis Res. Ther. 12(5):R192).

Anakinra (also known as Kineret®, Amgen): Anakinra is an IL1 receptor antagonist (So et al., 2007, Arthritis Res. Ther. 9(2):R28). Anakinra is a recombinant, non-glycosylated version of human IL1 receptor antagonist prepared from cultures of genetically modified E. coli. Anakinra blocks the biologic activity of naturally occurring IL1, by competitively inhibiting the binding of IL1 to the Interleukin-1 type receptor.

Interferon-gamma: known to selectively inhibit IL1β gene expression (Chujor et al., 1996, Eur. J. Immun. 26:1253-1259).

Pentoxifylline: a known inhibitor of the synthesis of IL1-β (Roy et al., 2007, J. Toxicol. Environ. Health B Crit. Rev. 10(4):235-57: Zargari, 2008, Dermat. Online J. 14(11): 2).

XOMA-052 (also known as gevokizumab): a potent anti-IL1β humanized neutralizing antibody (Owyang et al., 2011, mAbs 3(1):49-60; U.S. Pat. No. 7,531,116). XOMA-052 has a 300 femtomolar binding affinity for human IL1β and an in vitro potency in the low picomolar range. XOMA-052 is active in mouse models of acute gout.

K-832 (also known as 2-benzyl-5-(4-chlorophenyl)-6-[4-(methylthio)phenyl]-2H-pyridazin-3-one): this compound has high inhibitory activity against production of interleukin-1β (i.e., acts as an IL1β secretion inhibitor), and is being tested as a preventive and therapeutic drug for immune, inflammatory, and ischemic diseases (U.S. Pat. No. 6,348, 468; Tabunoki et al., 2003. Arthritis Rheum. 48 (Suppl. S555); Miura et al., 2010, Eur. J. Pharm. Biopharm. 76(2): 215-221).

CYT-013-IL1bQb (Cytos Biotechnology AG): an IL1β vaccine (ClinicalTrials.gov, NCT00924105: www dot clinicaltrials dot gov/ct2/show/NCT00924105).

LY-2189102 (Eli Lilly): a humanized IgG4 monoclonal anti-IL1β antibody in development for the treatment of diabetes, with a binding affinity of 2.8 pM, and a half-life and bioavailability of 20.3 days and 55%, respectively, after subcutaneous administration to healthy volunteers. LY2189102 was recently studied in a Phase II study in T2DM patients (CT registry NCT00942188; ClinicalTrials. gov., 2011, "A safety and pharmacokinetics study in patients with rheumatoid arthritis", at: www dot clinicaltrials dot gov/ct2/show/NCT00380744; ClinicalTrials dot gov., 2011. "A study for patients with rheumatoid arthritis on methotrexate (MTX) with an inadequate response to TNF inhibitor therapy", at: www dot clinicaltrials dot gov/ct2/show/ NCT00689728.

Further non-limiting examples of IL1β-depleting agents contemplated within the methods of the invention are any IL1β antibody, siRNA, ribozyme, antisense, aptamer, peptidomimetic, small molecule, and any combinations thereof.

Antibodies

The invention contemplates using a composition comprising an IL1β antibody within the methods of the invention. In certain embodiments, the antibody is selected from the group consisting of XOMA-052, AMG-108, canakinumab, rilonacept, LY-2189102, and any combinations thereof. In other embodiments, the antibody comprises an antibody selected from a polyclonal antibody, monoclonal antibody, humanized antibody, synthetic antibody, heavy chain antibody, human antibody, and biologically active fragment of an antibody.

It will be appreciated by one skilled in the art that an antibody comprises any immunoglobulin molecule, whether derived from natural sources or from recombinant sources, which is able to specifically bind to an epitope present on a target molecule. In certain embodiments, the target molecule comprises IL1β.

In one aspect of the invention, the target molecule is directly neutralized by an antibody that specifically binds to an epitope on the target molecule. In another aspect of the invention, the effects of the target molecule are blocked by an antibody that specifically binds to an epitope on a downstream effector. In still another aspect of the invention, the effects of the target molecule are blocked by an antibody that binds to an epitope of an upstream regulator of the target molecule.

When the antibody to the target molecule used in the compositions and methods of the invention is a polyclonal antibody (IgG), the antibody is generated by inoculating a suitable animal with a peptide comprising full length target protein, or a fragment thereof, an upstream regulator, or fragments thereof. These polypeptides, or fragments thereof, may be obtained by any methods known in the art, including chemical synthesis and biological synthesis, as described elsewhere herein. In this regard, exemplary IL1β sequences are SEQ ID NOs:1-2. Antibodies produced in the inoculated animal that specifically bind to the target molecule, or fragments thereof, are then isolated from fluid obtained from the animal.

Antibodies may be generated in this manner in several non-human mammals such as, but not limited to goat, sheep, horse, camel, rabbit, and donkey. Methods for generating polyclonal antibodies are well known in the art and are described, for example in Harlow et al., 1998, In: Antibodies, A Laboratory Manual, Cold Spring Harbor, N.Y.

Monoclonal antibodies directed against a full length target molecule, or fragments thereof, may be prepared using any well-known monoclonal antibody preparation procedures, such as those described, for example, in Harlow et al. (1998, In: Antibodies, A Laboratory Manual, Cold Spring Harbor, N.Y.) and in Tuszynski et al., 1988, Blood, 72:109-115. Human monoclonal antibodies may be prepared by the method described in U.S. Patent Publication No. 2003/0224490. Monoclonal antibodies directed against an antigen are generated from mice immunized with the antigen using standard procedures as referenced herein. Nucleic acid encoding the monoclonal antibody obtained using the procedures described herein may be cloned and sequenced using technology which is available in the art, and is described, for example, in Wright et al., 1992, Critical Rev. Immunol. 12(3,4): 125-168, and the references cited therein.

When the antibody used in the methods of the invention is a biologically active antibody fragment or a synthetic antibody corresponding to antibody to a full length target molecule, or fragments thereof, the antibody is prepared as follows: a nucleic acid encoding the desired antibody or fragment thereof is cloned into a suitable vector. The vector is transfected into cells suitable for the generation of large quantities of the antibody or fragment thereof. DNA encoding the desired antibody is then expressed in the cell thereby producing the antibody. The nucleic acid encoding the desired peptide may be cloned and sequenced using technology available in the art, and described, for example, in Wright et al., 1992, Critical Rev. in Immunol. 12(3,4): 125-168 and the references cited therein. Alternatively, quantities of the desired antibody or fragment thereof may also be synthesized using chemical synthesis technology. If the amino acid sequence of the antibody is known, the desired antibody can be chemically synthesized using methods known in the art as described elsewhere herein.

The present invention also includes the use of humanized antibodies specifically reactive with an epitope present on a target molecule. These antibodies are capable of binding to the target molecule. The humanized antibodies useful in the invention have a human framework and have one or more complementarity determining regions (CDRs) from an antibody, typically a mouse antibody, specifically reactive with a targeted cell surface molecule.

When the antibody used in the invention is humanized, the antibody can be generated as described in Queen et al. (U.S. Pat. No. 6,180,370), Wright et al., 1992, Critical Rev. Immunol. 12(3,4):125-168, and in the references cited therein, or in Gu et al., 1997, Thrombosis & Hematocyst 77(4):755-759, or using other methods of generating a humanized antibody known in the art. The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to humanized immunoglobulin coding sequences, including naturally-associated or heterologous promoter regions. The expression control sequences can be eukaryotic promoter systems in vectors capable of transforming or transfecting eukaryotic host cells, or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

Human constant region (CDR) DNA sequences from a variety of human cells can be isolated in accordance with well-known procedures. Preferably, the human constant region DNA sequences are isolated from immortalized B-cells as described in International Patent Application Publication No. WO 1987/02671. CDRs useful in producing the antibodies of the present invention may be similarly derived from DNA encoding monoclonal antibodies capable of binding to the target molecule. Such humanized antibodies may be generated using well-known methods in any convenient mammalian source capable of producing antibodies, including, but not limited to mice, rats, camels, llamas, rabbits, or other vertebrates. Suitable cells for constant region and framework DNA sequences and host cells in which the antibodies are expressed and secreted, can be obtained from a number of sources, such as the American Type Culture Collection, Manassas, Va.

One of skill in the art will further appreciate that the present invention encompasses the use of antibodies derived from camelid species. That is, the present invention includes, but is not limited to, the use of antibodies derived from species of the camelid family. As is well known in the art, camelid antibodies differ from those of most other mammals in that they lack a light chain, and thus comprise only heavy chains with complete and diverse antigen binding capabilities (Hamers-Casterman et al., 1993, Nature, 363:446-448). Such heavy-chain antibodies are useful in that they are smaller than conventional mammalian antibodies, they are more soluble than conventional antibodies, and further demonstrate an increased stability compared to some other antibodies. Camelid species include, but are not limited to Old World camelids, such as two-humped camels (*C. bactrianus*) and one humped camels (*C. dromedarius*). The camelid family further comprises New World camelids including, but not limited to llamas, alpacas, vicuna and guanaco. The production of polyclonal sera from camelid species is substantively similar to the production of polyclonal sera from other animals such as sheep, donkeys, goats, horses, mice, chickens, rats, and the like. The skilled artisan, when equipped with the present disclosure and the methods detailed herein, can prepare high-titers of antibodies from a camelid species. As an example, the production of antibodies in mammals is detailed in such references as Harlow et al., 1998. Antibodies: A Laboratory Manual, Cold Spring Harbor, N.Y.

$V_H$ proteins isolated from other sources, such as animals with heavy chain disease (Seligmann et al., 1979, Immunological Rev. 48:145-167, incorporated herein by reference in its entirety), are also useful in the compositions and methods of the invention. The present invention further comprises variable heavy chain immunoglobulins produced from mice and other mammals, as detailed in Ward et al., 1989, Nature 341:544-546 (incorporated herein by reference in its entirety). Briefly, $V_H$ genes are isolated from mouse splenic preparations and expressed in *E. coli*. The present invention encompasses the use of such heavy chain immunoglobulins in the compositions and methods detailed herein.

Antibodies useful as target molecule depletors in the invention may also be obtained from phage antibody libraries. To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA that specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al., 2001, Molecular Cloning: A Laboratory Manual, Cold Spring Harbor Laboratory Press, Cold Spring Harbor, N.Y.

Bacteriophage that encode the desired antibody may be engineered such that the protein is displayed on the surface thereof in such a manner that it is available for binding to its corresponding binding protein, e.g., the antigen against which the antibody is directed. Thus, when bacteriophage that express a specific antibody are incubated in the presence of a cell which expresses the corresponding antigen, the bacteriophage will bind to the cell. Bacteriophage that do not express the antibody will not bind to the cell. Such panning techniques are well known in the art and are described for example, in Wright et al., 1992, Critical Rev. Immunol. 12(3,4):125-168.

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage that display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CHI) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222:581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839: de Kruif et al., 1995, J. Mol. Biol. 248:97-105).

Once expressed, whole antibodies, dimers derived therefrom, individual light and heavy chains, or other forms of antibodies can be purified according to standard procedures known in the art. Such procedures include, but are not limited to, ammonium sulfate precipitation, the use of affinity columns, routine column chromatography, gel electrophoresis, and the like (see, generally, R. Scopes. "Protein Purification", Springer-Verlag, N.Y. (1982)). Substantially pure antibodies of at least about 90% to 95% homogeneity are preferred, and antibodies having 98% to 99% or more homogeneity most preferred for pharmaceutical uses. Once purified, the antibodies may then be used to practice the method of the invention, or to prepare a pharmaceutical composition useful in practicing the method of the invention.

The antibodies of the present invention can be assayed for immunospecific binding by any method known in the art. The immunoassays that can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g. Current Protocols in Molecular Biology, (Ausubel et al., eds.), Greene Publishing Associates and Wiley-Interscience, New York (2002)). Exemplary immunoassays are described briefly below (but are not intended to be in any way limiting).

Methods

The invention includes a method of killing, and/or preventing or reducing the growth of, a prostate cancer cell that does not express androgen receptor [AR(−) PC cell]. In certain embodiments, the method comprises contacting the AR(−) PC cell with an effective amount of an IL1β-depleting agent, whereby the cell is killed and/or growth of the cell is prevented or reduced.

In certain embodiments, the cell is in vitro or ex vivo. In other embodiments, the cell is part of a solid tumor within a subject. In yet other embodiments, the solid tumor comprises a prostate tumor. In yet other embodiments, the solid tumor comprises a bone metastasis. In yet other embodiments, the cell is mammalian. In yet other embodiments, the cell is human.

The invention further includes a method of treating or preventing metastasis of a AR(−) PC cell in a subject. In certain embodiments, the method comprises administering to the subject a therapeutically effective amount of an IL1β-depleting agent, whereby metastasis of the AR(−) PC cell in the subject is treated or prevented.

The invention further includes a method of treating or preventing bone metastasis of a prostate cancer cell that expresses androgen receptor and does not express IL1β [AR(+)/IL1β(−) PC cell] in a subject. In certain embodiments, the method comprises administering to the subject a therapeutically effective amount of an IL1β-depleting agent, whereby bone metastasis of the cell in the subject is treated or prevented.

In certain embodiments, the metastasis comprises bone metastasis. In other embodiments, the subject suffers from castration-resistant prostate cancer. In yet other embodiments, the subject is further administered at least one additional compound selected from the group consisting of a chemotherapeutic agent and anti-cell proliferation agent. In yet other embodiments, the IL1β-depleting agent and the at least one additional compound are co-administered to the subject. In yet other embodiments, the IL1β-depleting agent and the at least one additional compound are co-formulated and co-administered to the subject. In yet other embodiments, the IL1β-depleting agent is administered to the subject by an administration route selected from the group consisting of inhalational, oral, rectal, vaginal, parenteral, topical, transdermal, pulmonary, intranasal, buccal, ophthalmic, intrathecal, and any combinations thereof. In yet other embodiments, the subject is a mammal. In yet other embodiments, the mammal is a human.

The invention further includes a method of recommending anti-metastasis therapeutic treatment for a subject suffering from prostate cancer. In certain embodiments, the method comprises determining whether a biological sample from the subject comprises a AR(+)/IL1β(−) PC cell or a AR(−) PC cell, wherein, if the biological sample from the subject comprises a AR(+)/IL1β(−) PC cell or a AR(−) PC cell, the subject is instructed to undergo anti-metastatic therapeutic treatment using a therapeutically effective amount of an IL1β-depleting agent. In other embodiments, the subject is instructed not to undergo androgen-deprivation therapy (ADT).

The invention further provides a method of identifying a prostate cancer patient who will benefit from an anti-metastasis therapeutic treatment comprising an IL1β-depleting agent. In certain embodiments, the method comprises assessing in a biological sample of the patient the level of at least one marker selected from the group consisting of: PCADM-1, antibody that binds to PCADM-1, and polynucleotide encoding PCADM-1; and comparing the level of the at least one marker in the patient's biological sample with the level of the at least one marker in a biological sample obtained from a like mammal not afflicted with metastatic prostate cancer, wherein a higher level of the at least one marker in the patient's biological sample as compared to the level of the at least one marker in the like mammal's biological sample indicates that the patient will benefit from anti-metastatic therapeutic treatment comprising an IL1β-depleting agent.

The invention further provides a method of determining if a prostate cancer patient is benefiting from an anti-metastasis therapeutic treatment comprising an IL1β-depleting agent. In certain embodiments, the method comprises assessing, in at least first and second biological samples of the patient, the level of at least one marker selected from the group consisting of: PCADM-1, antibody that binds to PCADM-1, and polynucleotide encoding PCADM-1; wherein (i) the first sample is obtained before the patient is administered an IL1β-depleting agent, and the second sample is obtained after the patient is administered an IL1β-depleting agent, or (ii) the first sample and second samples are obtained after the patient is administered an IL1β-depleting agent, the second sample being obtained at a later time point of the treatment; and comparing the levels of the at least one marker in the patient's at least first and second biological samples, wherein a lower level of the at least one marker in the patient's second biological sample as compared to the level of the at least one marker in the patient's first biological sample indicates that the patient is responding to the anti-metastatic therapeutic treatment comprising an IL1β-depleting agent, and wherein an equal or higher level of the at least one marker in the patient's second biological sample as compared to the level of the at least one marker in the patient's first biological sample indicates that the patient is not responding to the anti-metastatic therapeutic treatment comprising an IL1β-depleting agent.

In certain embodiments, the antibody binds specifically to PCADM-1 and does not cross-react non-specifically with human S2 ribosomal protein. In other embodiments, the method further comprises instructing the patient to undergo anti-metastasis therapeutic treatment comprising an IL1β-depleting agent. In yet other embodiments, the method further comprises administering to the patient anti-metastasis therapeutic treatment comprising an IL1β-depleting agent.

In certain embodiments, the patient is responding to the anti-metastatic therapeutic treatment comprising an IL1β-depleting agent, and wherein the subject is instructed to maintain the therapeutic treatment comprising an IL1β-depleting agent treatment. In other embodiments, the patient is not responding to the anti-metastatic therapeutic treatment comprising an IL1β-depleting agent, and wherein the subject is instructed to discontinue the therapeutic treatment comprising an IL1β-depleting agent treatment.

A biological sample can be a tissue sample, a biological fluid sample, a cell (e.g., a tumor cell) sample, and the like.

Any means of sampling from a subject, for example, tissue biopsy, by blood draw, spinal tap, tissue smear or scrape can be used to obtain a biological sample. Thus, the biological sample can be a biopsy specimen (e.g., tumor, polyp, mass (solid, cell)), aspirate, smear or blood sample. The biological sample can be a tissue from an organ that has a tumor (e.g., cancerous growth) and/or tumor cells, or is suspected of having a tumor and/or tumor cells. A tumor sample can also be obtained by in vitro harvest of cultured human cells derived from an individual's tissue. Tumor samples can, if desired, be stored before analysis by suitable storage means that preserve a sample's protein and/or nucleic acid in an analyzable condition, such as quick freezing, or a controlled freezing regime.

Kits

The invention includes a kit comprising an IL1β-depleting agent, and an instructional material for use thereof. The instructional material included in the kit comprises instructions for preventing or treating preventing metastasis of a AR(−) PC cell or AR(+)/IL1β(−) PC cell. In certain embodiments, the primary cancer comprises prostate cancer. In other embodiments, the metastasis comprises bone metastasis. In yet other embodiments, the IL1β-depleting agent is selected from the group consisting of anakinra, XOMA-052, AMG-108, canakinumab, rilonacept, K-832, CYT-013-IL1bQb, LY-2189102, dexamethasone, interferon-gamma, pentoxifylline, IL1β antibody, siRNA, ribozyme, antisense, aptamer, peptidomimetic, small molecule, and any combinations thereof.

Combination Therapies

The compounds identified using the methods described here are useful in the methods of the invention in combination with at least one additional compound useful for treating cancer. This additional compound may comprise compounds identified herein or compounds, e.g., commercially available compounds, known to treat, prevent, or reduce the symptoms of cancer and/or metastasis.

In one aspect, the present invention contemplates that the agents useful within the invention may be used in combination with a therapeutic agent such as an anti-tumor agent, including but not limited to a chemotherapeutic agent, an anti-cell proliferation agent or any combination thereof. For example, any conventional chemotherapeutic agents of the following non-limiting exemplary classes are included in the invention: alkylating agents; nitrosoureas; antimetabolites; antitumor antibiotics; plant alkyloids; taxanes; hormonal agents; and miscellaneous agents.

Alkylating agents add alkyl groups to many electronegative groups under conditions present in cells, thereby interfering with DNA replication to prevent cancer cells from reproducing. Most alkylating agents are cell cycle non-specific. In specific aspects, they stop tumor growth by cross-linking guanine bases in DNA double-helix strands. Non-limiting examples include busulfan, carboplatin, chlorambucil, cisplatin, cyclophosphamide, dacarbazine, ifosfamide, mechlorethamine hydrochloride, melphalan, procarbazine, thiotepa, and uracil mustard.

Anti-metabolites prevent incorporation of bases into DNA during the synthesis (S) phase of the cell cycle, prohibiting normal development and division. Non-limiting examples of antimetabolites include drugs such as 5-fluorouracil, 6-mercaptopurine, capecitabine, cytosine arabinoside, floxuridine, fludarabine, gemcitabine, methotrexate, and thioguanine.

Antitumor antibiotics generally prevent cell division by interfering with enzymes needed for cell division or by altering the membranes that surround cells. Included in this class are the anthracyclines, such as doxorubicin, which act to prevent cell division by disrupting the structure of the DNA and terminate its function. These agents are cell cycle non-specific. Non-limiting examples of antitumor antibiotics include dactinomycin, daunorubicin, doxorubicin, idarubicin, mitomycin-C, and mitoxantrone.

Plant alkaloids inhibit or stop mitosis or inhibit enzymes that prevent cells from making proteins needed for cell growth. Frequently used plant alkaloids include vinblastine, vincristine, vindesine, and vinorelbine. However, the invention should not be construed as being limited solely to these plant alkaloids.

The taxanes affect cell structures called microtubules that are important in cellular functions. In normal cell growth, microtubules are formed when a cell starts dividing, but once the cell stops dividing, the microtubules are disassembled or destroyed. Taxanes prohibit the microtubules from breaking down such that the cancer cells become so clogged with microtubules that they cannot grow and divide. Non-limiting exemplary taxanes include paclitaxel and docetaxel.

Hormonal agents and hormone-like drugs are utilized for certain types of cancer, including, for example, leukemia, lymphoma, and multiple myeloma. They are often employed with other types of chemotherapy drugs to enhance their effectiveness. Sex hormones are used to alter the action or production of female or male hormones and are used to slow the growth of breast, prostate, and endometrial cancers. Inhibiting the production (aromatase inhibitors) or action (tamoxifen) of these hormones can often be used as an adjunct to therapy. Some other tumors are also hormone dependent. Tamoxifen is a non-limiting example of a hormonal agent that interferes with the activity of estrogen, which promotes the growth of breast cancer cells. Treatment of prostate cancer may also involve hormone treatment (also called androgen deprivation therapy or androgen suppression therapy). Prostate cancer may grow when exposed to the male hormone testosterone and its related hormones, called androgens. Hormone treatment for prostate cancer stops the production of testosterone and all androgens either temporarily or permanently. Drugs can stop the testicles from producing testosterone and protect cells from any other androgens that remain in the body. Hormone medications may include: various hormones such as estrogen to counter the effects of testosterone; drugs that lower testosterone levels or block the activity of male hormones in the body, such as antiandrogen agents, lutenizing hormone-releasing hormone (LHRH) analogs, or agonists, and agents that block the production of androgens by the adrenal glands; combined hormone therapy that decreases testosterone production from the testicles, as well as from glands located on the kidneys, called adrenal glands, that produce hormones. Hormone treatment may also include surgical removal of the testicles (called orchiectomy) where testosterone is produced. This prevents male hormones from further stimulating the growth of the prostate cancer.

Miscellaneous agents include chemotherapeutics such as bleomycin, hydroxyurea. L-asparaginase, and procarbazine that are also useful in the invention.

An anti-cell proliferation agent can further be defined as an apoptosis-inducing agent or a cytotoxic agent. The apoptosis-inducing agent may be a granzyme, a Bcl-2 family member, cytochrome C, a caspase, or a combination thereof. Exemplary granzymes include granzyme A, granzyme B, granzyme C, granzyme D, granzyme E, granzyme F, granzyme G, granzyme H, granzyme I, granzyme J, granzyme K, granzyme L, granzyme M, granzyme N, or a combination thereof. In other specific aspects, the Bcl-2 family member is, for example, Bax, Bak, Bcl-Xs, Bad, Bid, Bik, Hrk, Bok, or a combination thereof. In additional aspects, the caspase is caspase-1, caspase-2, caspase-3, caspase-4, caspase-5, caspase-6, caspase-7, caspase-8, caspase-9, caspase-10, caspase-11, caspase-12, caspase-13, caspase-14, or a combination thereof. In specific aspects, the cytotoxic agent is TNF-α, gelonin, Prodigiosin, a ribosome-inhibiting protein (RIP), *Pseudomonas* exotoxin, *Clostridium difficile* Toxin B, *Helicobacter pylori* VacA, *Yersinia enterocolitica* YopT, Violacein, diethylenetriaminepentaacetic acid, irofulven, Diptheria Toxin, mitogillin, ricin, botulinum toxin, cholera toxin, saporin 6, or a combination thereof.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Pharmaceutical Compositions and Formulations

The invention envisions the use of a pharmaceutical composition comprising an IL1β-depleting agent within the methods of the invention.

Such a pharmaceutical composition is in a form suitable for administration to a subject, or the pharmaceutical composition may further comprise one or more pharmaceutically acceptable carriers, one or more additional ingredients, or some combination of these. The various components of the pharmaceutical composition may be present in the form of a physiologically acceptable salt, such as in combination with a physiologically acceptable cation or anion, as is well known in the art.

In an embodiment, the pharmaceutical compositions useful for practicing the method of the invention may be administered to deliver a dose of between 1 ng/kg/day and 100 mg/kg/day. In other embodiments, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration is readily apparent to the skilled artisan and depends upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it is understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In certain embodiments, the compositions are formulated using one or more pharmaceutically acceptable excipients or carriers. In certain embodiments, the pharmaceutical compositions comprise a therapeutically effective amount of at least IL1β-depleting agent and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences, 1991, Mack Publication Co., New Jersey.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers: salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent, which inhibit the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount ranging from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition, which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives (e.g., sodium carboxymethylcellulose, hydroxypropylmethylcellulose, methylcellulose). Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one that comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Administration/Dosing

The regimen of administration may affect what constitutes an effective amount. For example, the therapeutic formulations may be administered to the patient either prior to or after a surgical intervention related to cancer, or shortly after the patient was diagnosed with cancer. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat cancer in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon any number of factors, such as, but not limited to, the type and severity of the disease being treated, and the type and age of the animal.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated, each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of cancer in a patient.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds of the invention for administration may be in the range of from about 1 µg to about 7,500 mg, about 20 µg to about 7,000 mg, about 40 µg to about 6,500 mg, about 80 µg to about 6,000 mg, about 100 µg to about 5,500 mg, about 200 µg to about 5,000 mg, about 400 µg to about 4,000 mg, about 800 µg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments therebetween.

In some embodiments, the dose of a compound of the invention is from about 0.5 µg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of cancer in a patient.

The term "container" includes any receptacle for holding the pharmaceutical composition. For example, In certain embodiments, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing cancer in a patient.

Routes of Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose: granulating and disintegrating agents such as cornstarch: binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compounds of the invention may be in the form of tablets or capsules prepared by conventional means with pharmaceutically acceptable excipients such as binding agents; fillers: lubricants; disintegrates; or wetting agents. If desired, the tablets may be coated using suitable methods and coating materials such as OPADRY™ film coating systems available from Colorcon. West Point, Pa. (e.g., OPADRY™ OY Type, OYC Type. Organic Enteric OY-P Type, Aqueous Enteric OY-A Type, OY-PM Type and OPADRY™ White, 32K18400).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g. methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds useful within the methods of the invention, and a further layer providing for the immediate release of one or more compounds useful within the methods of the invention. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

Controlled- or sustained-release formulations of a pharmaceutical composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form. For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation. In a preferred embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours. The term pulsatile release is used herein in its conventional sense to refer to a drug formulation that provides release of the drug in such a way as to produce pulsed plasma profiles of the drug after drug administration. The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples.

These Examples are provided for the purpose of illustration only, and the invention is not limited to these Examples, but rather encompasses all variations that are evident as a result of the teachings provided herein.

Materials and Methods

Cell Lines and Culture

DU-145, 22Rv1. LNCaP, and VCaP human prostate cancer cell lines were purchased from ATCC: the PC3-ML cell line was derived from the parental PC-3 cell line as described in Wang M, Stearns M E, Isolation and characterization of PC-3 human prostatic tumor sublines which preferentially metastasize to select organs in S.C.I.D. mice. Differentiation. 1991; 48:115-25. All cell lines were authenticated by short tandem repeat profiling by IDEXX Radil and/or DDC Medical. Cells were cultured in Dulbecco's Modified Eagle Medium (DU-145, VCaP, and PC3-ML) or RPMI-1460 (22Rv1 and LNCaP) containing 10% fetal bovine serum and 0.1% gentamicin. Bone marrow-derived Human Mesenchymal Stem cells (Lonza) were used between passage 5 and 8 and cultured in α-MEM supplemented with 10% FBS, 1 ng/ml bFGF (R&D), and 0.1% gentamicin. Each cell line was cultured at 37° C. and 5% $CO_2$ and discarded 10 passages following thawing. Conditioned media experiments were performed as described in Liu Q, Russell M R. Shahriari K, Jemigan D L, Lioni M I, Garcia F U, et al. Interleukin-1β promotes skeletal colonization and progression of metastatic prostate cancer cells with neuroendocrine features. Cancer Res. 2013; 73:3297-305.

Viral Vectors for Stable Gene Expression

Stable expression of the fluorescent markers eGFP and mCherry, the luciferase enzymes Red Firefly Luciferase and Luc2, and the cytokine IL-1β were achieved through lentiviral transduction with the following constructs: pLenti CMV GFP Blast (659-1), pLenti CMV Blast empty (w263-1), pLenti CMV Puro DEST (wI 18-1), and pENTRIA no ccDB (w48-1) were gifts from Eric Campeau (Addgene plasmids #17445, 17486, 17452, and 17398). pLenti CMV mCherry Blast was produced by subcloning the mCherry gene from pmCherry-N1 (Clontech. Mountain View, Calif., USA) into the BamHI and XbaI sites of pLenti CMV Blast empty. pLenti CMV Red Luc Puro and pLenti CMV Luc2 Puro were produced by first subcloning the Red Firefly Luciferase gene from pMCS-Red Firefly Luc (Thermo Fisher Scientific, Waltham, Mass., USA) or the Luc2 gene from pGL4.51[luc2/CMV/Neo] (Clontech) into the BamHI and XhoI sites of pENTR1 A no ccDB; pLenti CMV IL-1β Puro was produced by initially shuttling human IL-1β cDNA (NM_000576) into the SalI and BamHI sites of pENTRA1 A no ccdB. Each of these inserts was then transferred via Gateway LR Clonase II (Invitrogen) into pLenti CMV Puro DEST. Following lentiviral transduction, cells were selected with puromycin or blasticidin for one week at the following concentrations, respectively: PC3-ML: 600 ng/mL, 5 µg/mL; 22Rv1: 1 µg/mL, 6 µg/mL; DU-145: 500 ng/mL, 10 µg/mL, LNCaP: 2 µg/mL, 7 µg/mL; VCaP: 2 µg/mL, 7 µg/mL.

SDS-PAGE and Western Blotting

Cell lysates were obtained and Western Blotting analysis was performed as previously described. Primary antibodies were diluted in TBST and incubated overnight at 4° C. HRP-conjugated secondary antibodies were used at 3.33 ng/ml. Chemiluminescent signals were obtained using SuperSignal West Femto substrate (Pierce) and detected with the Fluorochem 8900 imaging system and related software. Primary antibodies and dilutions used for Western Blotting were those targeting S100 A4 at 1:500 (ab27957, Abeam); IL-1 at 1:250 (SC-7884, Santa Cruz Biotechnology) Actin at 1:3000 (A-2066. Sigma-Aldrich); phospho-IκBα Scr32 at 1:500 (#2859), IκBα at 1:500 (#4814), phospho-NF-κB p65 Ser536 at 1:1000 (#3033), NF-κB p65 at 1:1000 (#8242), and GAPDH at 1:5000 (#5174), all from Cell Signaling Technology.

Immunofluorescence

Formalin-Fixed Paraffin-Embedded (FFPE) sections of primary PCa and bone metastases were obtained from the archives of the Department of Pathology at Drexel University College of Medicine and stained using a FITC-conjugated Pan-Cytokeratin antibody (clone C-11) and an antibody against the N-20 region of the human Androgen Receptor and then imaged using an Axio Scope A1 microscope (Zeiss) paired with the Nuance Multispectral Imaging System (PerkinElmer). hMSCs cells were seeded onto glass coverslips, treated, fixed in 4% paraformaldehyde and stained with Anti-Actin, α-Smooth Muscle—Cy3™ (clone 1 A4). Samples were mounted with DAPI-contained medium and imaged with an LSM 5 Exciter—Axio Imager Z1m confocal microscope (Zeiss).

Animal Models

Male C.B17-SC mice (Taconic) at six to eight weeks of age were anesthetized with ketamine (80 mg/kg) and xylazine (10 mg/kg) prior being inoculated with cancer cells via the left cardiac ventricle. For anakinra treatment, animals received an initial subcutaneous dose of vehicle (PBS) or anakinra (Swedish Orphan Biovitrum) 24 hours prior to cancer cell inoculation, then additional doses at the time of xenograft and daily thereafter until sacrifice.

Generation of IL-1R SCID Mice

IL-1R SCID mice were generated by crossing CB17-SC RF mice with transgenic animals knockout for IL-1R1 (OMIM 147810, a gift from Dr. Nancy McNamara, UCSF). These animals were then genotyped for the Prkdc$^{scid}$ mutation by PCR using the forward primer (SEQ ID NO: 4): 5' GGA AAA GAA TTG GTA TCC AC 3' and reverse (SEQ ID NO: 5): 5' AGT TAT AAC AGC TGG GTT GGC 3': the product was digested with AluI resulting in fragments of 68 and 11 bp (wild-type) and 38, 28, and 11 bp (SCID). IL-1R status was determined by multiplex PCR using the following primers: IL-1R WT (SEQ ID NO: 6): Fwd—5' CCA CAT ATT CTC CAT CAT CTC TGC TGG TA 3', IL-1R WT (SEQ ID NO: 7): Rev—5' TTT CGA ATC TCA GTT GTC AAG TGT GTC CC 3', IL-1R KO (SEQ ID NO: 8): Fwd—5' CTG AAT GAA CTG CAG GAC GA 3'. IL-1R KO (SEQ ID NO: 9): Rev—5' ATA CTT TCT CGG CAG GAG CA 3', and resulting in amplification of fragments of 350 base pairs (wild-type allele) and 172 base pairs (knockout). Once animals homozygous for Prkdc$^{scid}$ and heterozygous for IL-1R were obtained the colony was maintained through intercross of IL-1R heterozygotes, with six- to eight-week-old male wild-type and knockout littermates used for the experiments.

In Vivo Bioluminescence Imaging

Prior to each weekly imaging session, animals were injected IP with 150 mg/kg D-Luciferin (PerkinElmer) and allowed to rest for ten minutes, then anesthetized using 3% isoflurane and transferred to the chamber of an IVIS Lumina XR (PerkinElmer), where they received 2% isoflurane throughout image acquisition. Fifteen minutes after injection of the substrate, exposures of both dorsal and ventral views were acquired both without an emission filter and with the 515-575 nm band pass filter; at the end of each experiment, radiographs were taken of each animal. Analysis of these data was performed using Living Image software, v4.3.

Processing of animal tissues.

Bones and soft tissue organs were collected and processed as described previously. All sections spanning the entire bone width (approximately 32 for femur and tibia) were inspected to obtain accurate enumeration of DTCs as well as visualization and size measurement of tumor foci in the inoculated animals.

Fluorescence Microscopy and Morphometric Analysis of Animal Metastases

Fluorescent images of skeletal metastases were collected as described in Liu et al., 2013, Cancer Res. 73:3297-305. In experiments assessing arrival/colonization of the bone, animals were sacrificed and femora and tibia were imaged and processed using Nuance software and a standardized spectral library and total GFP-positive DTCs counted in the knee joint of each animal. Lung tissues from the same animals were sectioned at 80 µm at intervals across the organ and images of five random fields analyzed as described. Data from both tumor measurements and DTC counts were subjected to statistical analysis between groups using an unpaired, two-tailed Student's t-test.

Immunohistochemistry and Analysis of Human Bone Metastases

De-identified FFPE biopsy specimens of bone metastatic lesions from two different cohorts of ADT-treated advanced prostate cancer patients were obtained from the archives of the Departments of Pathology at Drexel University College of Medicine (5 patients) and at Thomas Jefferson University (4 patients), and stained using the aforementioned antibody against the N-20 region of the human Androgen Receptor, or against Prostein (Clone 10E3). These biopsy specimens were used to determine the relative percentage of AR+ and AR− PCa cells across 43 distinct regions of interest. Two certified pathologists (F.U.G and Y.G) selected the tumor areas to be inspected for AR expression by examining paired serial sections stained with Hematoxylin/Eosin. Assessment of AR staining intensity was performed using the Aperio system and ImageScope software (Leica). Immunohistochemistry signals were digitized and analyzed by scoring staining intensity.

Example 1: Expression of Androgen Receptor in Prostate Cancer Cells

Figure 1B:
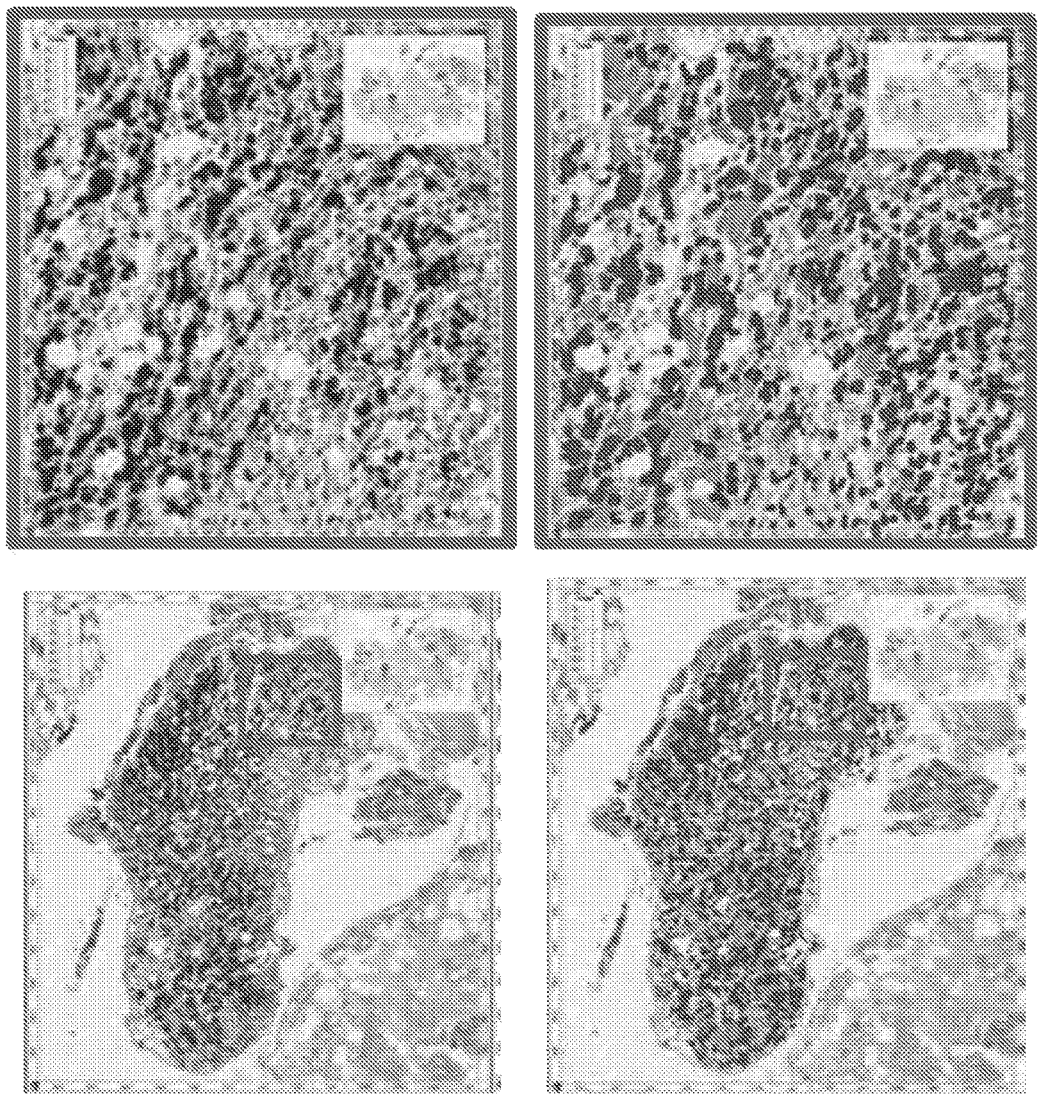
FIG. 1B is a set of images of illustrating immunochemistry detection of a primary antibody against AR using the Aperio Imaging and analysis suite.
Figure 1C:
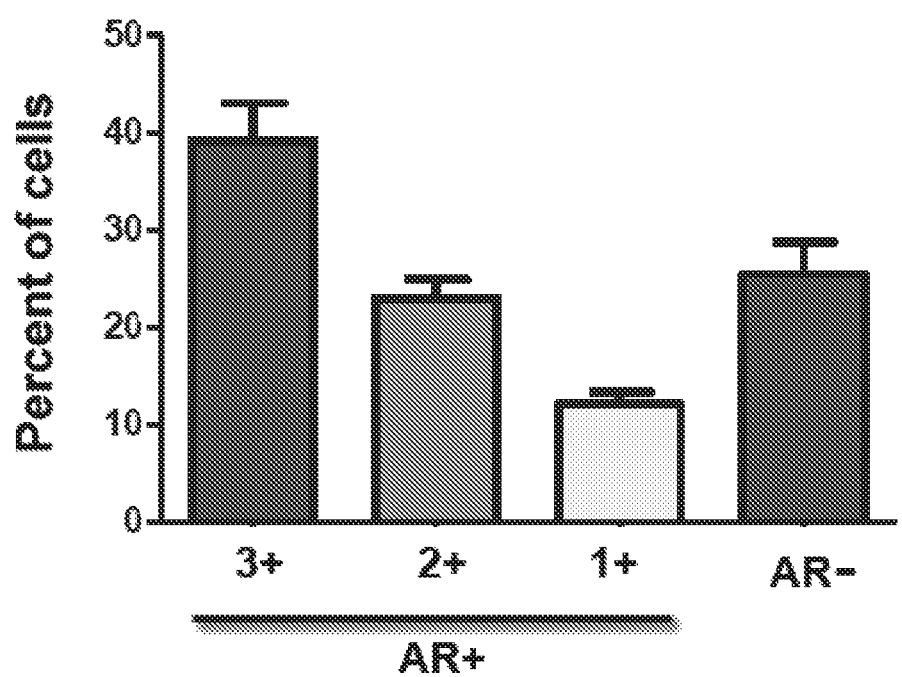
FIG. 1C is a set of bar graphs illustrating quantitation of AR(+) and AR(−) cells in metastatic lesions.
Figure 1D:
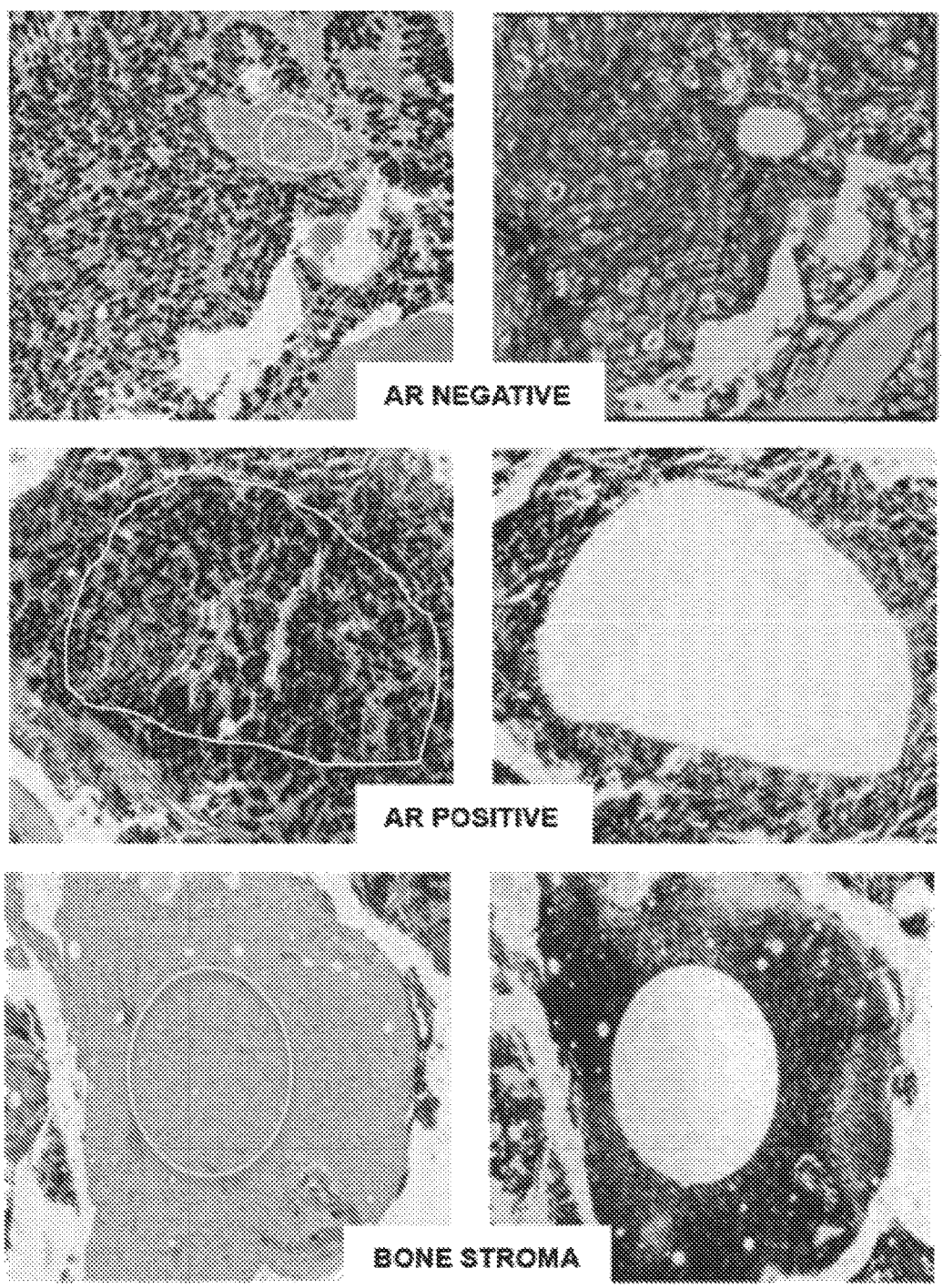
FIG. 1D is a series of images illustrating results obtained by harvesting tissues from bone metastatic lesions by laser capture microdissection (LCM).

As demonstrated in FIG. 1A, prostate cancer cells lacking the expression of the Androgen Receptor (AR) were detected in metastatic lesions at the skeletal level. The signal generated by the immunochemistry detection of a primary antibody against AR (1-20 amino acids, custom made by Bethyl Laboratories) was used to establish the percentage of AR (+) and AR(−) cells using the Aperio Imaging and analysis suite (FIG. 1B). The present data showed that metastatic lesions include approximately one third of AR(−) cells (FIG. 1D).

Figure 1E:
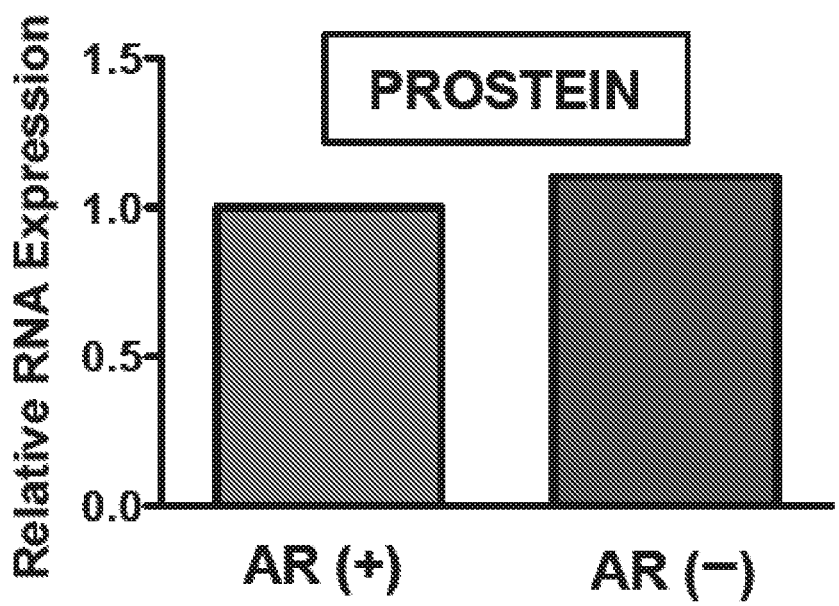
FIGS. 1E-1H are a set of bar graphs illustrating qRT-PCR quantitation of various proteins or receptors in AR(−) and AR(+) cells.
Figure 1F:
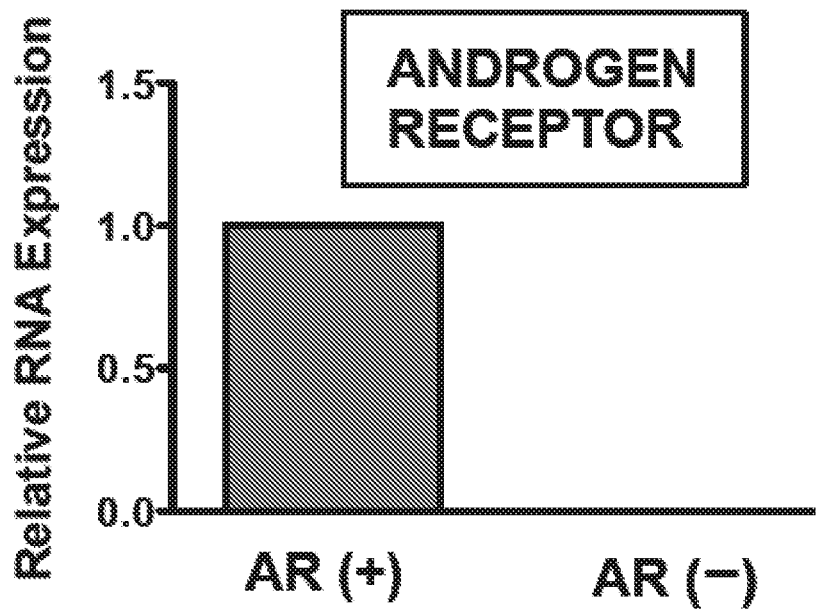
Figure 1G:
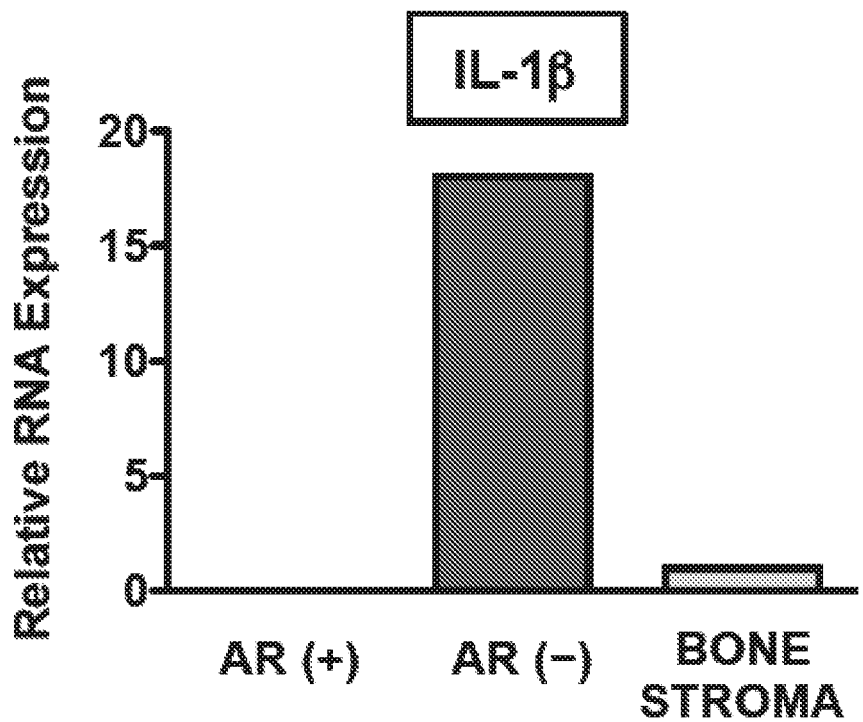
Figure 1H:
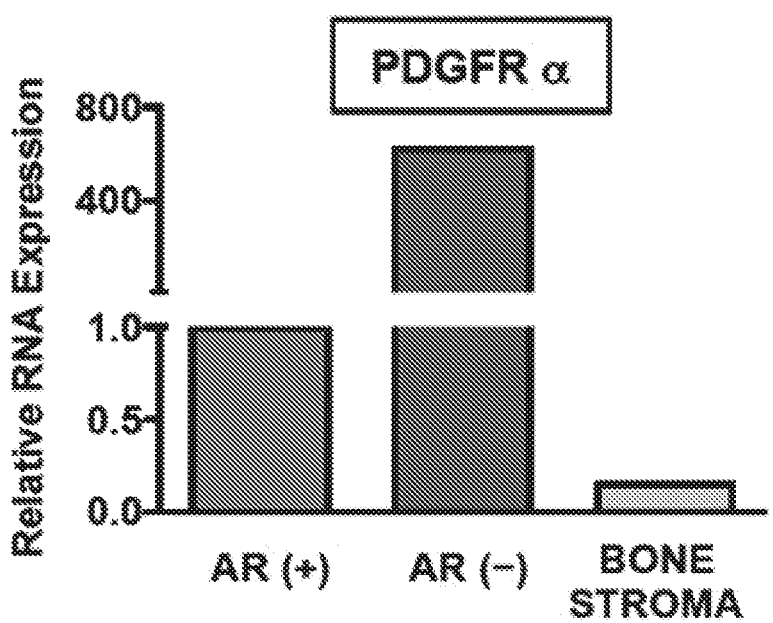
Figure 1I:
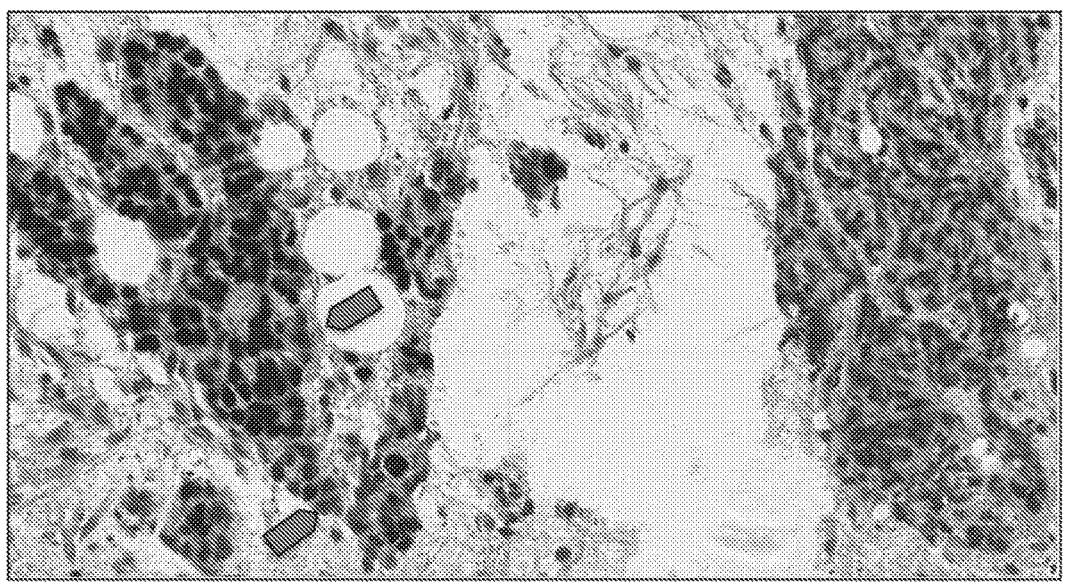
FIG. 1I is an image of an AR stained bone biopsy of a patient with documented post-ADT metastatic CRPC. Cancer cells lacking nuclear AR were commonly detected intermixed with AR+ cells (left hand side, indicated by arrows); in all specimen, large areas composed almost entirely of cells lacking nuclear AR staining were observed (right hand side).
Figure 1J:
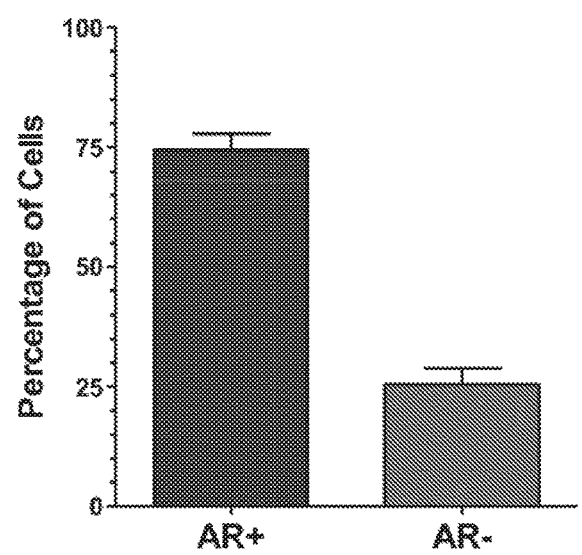
FIG. 1J is a bar graph illustrating that the fraction of cancer cells negative for AR expression was found to be 27±2%, with the percentage of infiltrating or resident non-cancerous cells (immune, endothelial or stromal origin) not exceeding 1-2%.
Figure 1K:
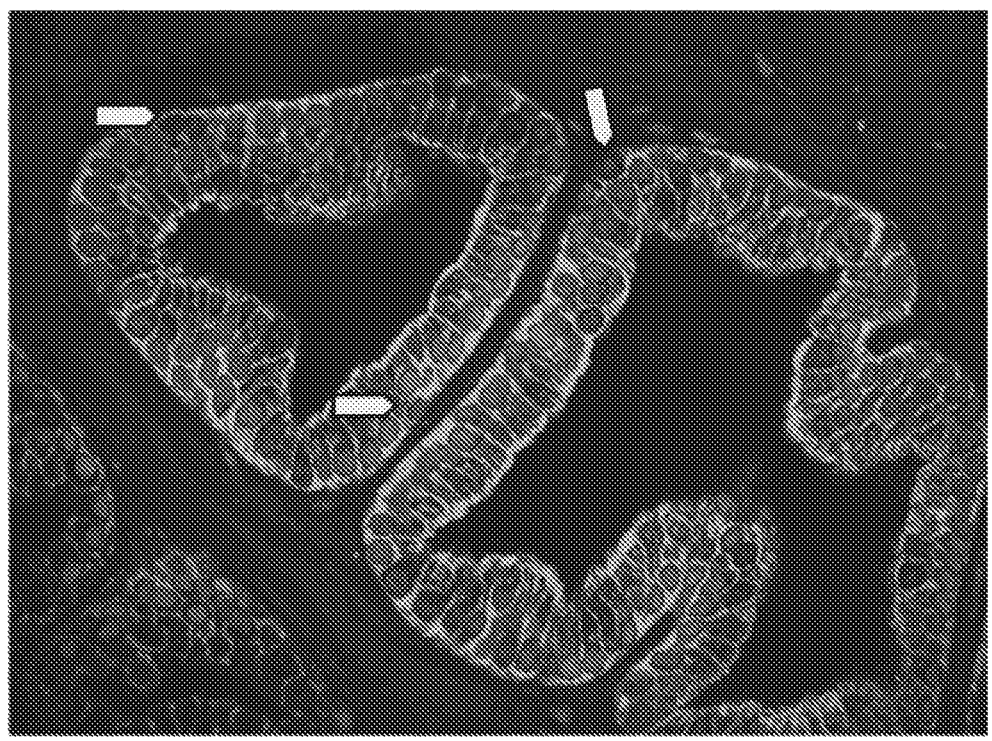
FIG. 1K-1L are images of primary (FIG. 1K) and bone metastatic (FIG. 1L) tissues, stained with both a pan-cytokeratin antibody and an AR antibody. Both AR+(denoted by arrows in FIG. 1K and the three arrows in the lighter region of FIG. 1L) and AR− (denoted by arrows in darker region in FIG. 1L) cancer cells are of epithelial origin and are present in the basal compartment of primary tumors as well as mixed with AR+ cells in skeletal. Non-epithelial AR− cells were identified in the bone marrow stroma (denoted by arrows in darker region in FIG. 1L)
Figure 1L:
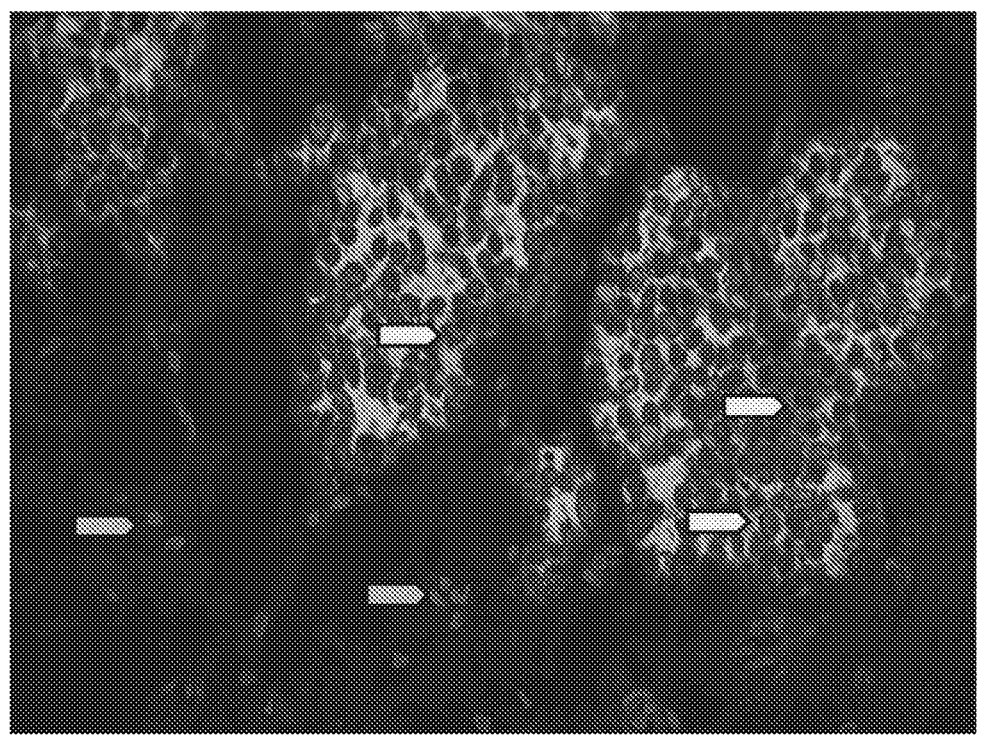

In order to assess the AR status of PCa cells colonizing the skeleton, we examined archival bone biopsies obtained from nine patients in two different clinical cohorts and with documented post-ADT metastatic CRPC. These specimens revealed remarkable variability of AR staining, ranging from lowest to highest signal intensity even within individual lesions (FIG. 1L), while in some areas the AR could be detected in only a minority of cancer cells (FIG. 1L). Overall, more than 25% of cancer cells identified by morphological and histopathological criteria in these patients did not stain for AR (FIG. 1J). Furthermore, dual immunofluorescence staining with an AR and a pan-cytokeratin antibody confirmed that the cancer cells identified in these metastatic lesions, both with and without AR expression, were indeed of epithelial origin, as can be seen at both primary (FIG. 1K) and bone metastatic sites (FIG. 1L).

To further validate the immunohistochemistry data, tissues were harvested from bone metastatic lesions by Laser Capture Microdissection (LCM) (FIG. 1D), and qRT-PCR was used to evaluate the expression of the prostate-specific antigen protein, which was equally detected in prostate cancer cells independently of their AR status. These results clearly demonstrate that AR(−) cancer cells detected in skeletal metastases from prostate cancer patients are indeed of prostatic origin (FIGS. 1E-1F). Furthermore, the present studies indicate that the cytokine IL1β is exclusively expressed by AR(−) cancer cells (FIG. 1G), which also express higher levels of the alpha-receptor for Platelet-Derived Growth Factor (PDGFR-α) as compared to AR(+) cells (FIG. 1H).

Example 2: Investigation of Castration-Resistant Prostate Cancer

The emergence of AR(−) prostate cancer cells is considered a late event in the clinical history of prostate cancer and occurring as a consequence of Androgen-Deprivation Therapy (ADT). Patients that have received local treatments for their prostate tumors (surgery and/or radiation therapy) are monitored for Prostate Specific Antigen (PSA) in the blood. If the extremely low levels of PSA following local treatment are found to increase, this is defined as "biochemical failure" and associated with a recurrence of the prostate neoplasia. In the absence of evidence for local recurrence, it is then assumed that the patient has distant microscopic recurrences even in the absence of evident metastatic disease. At this point, several measures are undertaken to bring the levels of circulating androgens to castrate-like levels, in an attempt to counteract the translational activity of the AR, which depends on androgens and fuels the growth of prostate cancer cells. The ADT is effective for approximately 16-24 months, after which the disease becomes Castration-Resistant (CRPC). While CRPC is not attributed to the lack of AR in cancer cells, AR(−) are commonly detected in secondary tumors that start to appear in soft-tissues, such as liver and lung. These cells are considered transitioning toward a Neuroendocrine (NE) phenotype as a result of ADT, resembling cells detected in approximately 0.5% of primary prostate tumors that originally derive from the few neuroendocrine cells that exist in the prostate gland.

Figure 2:
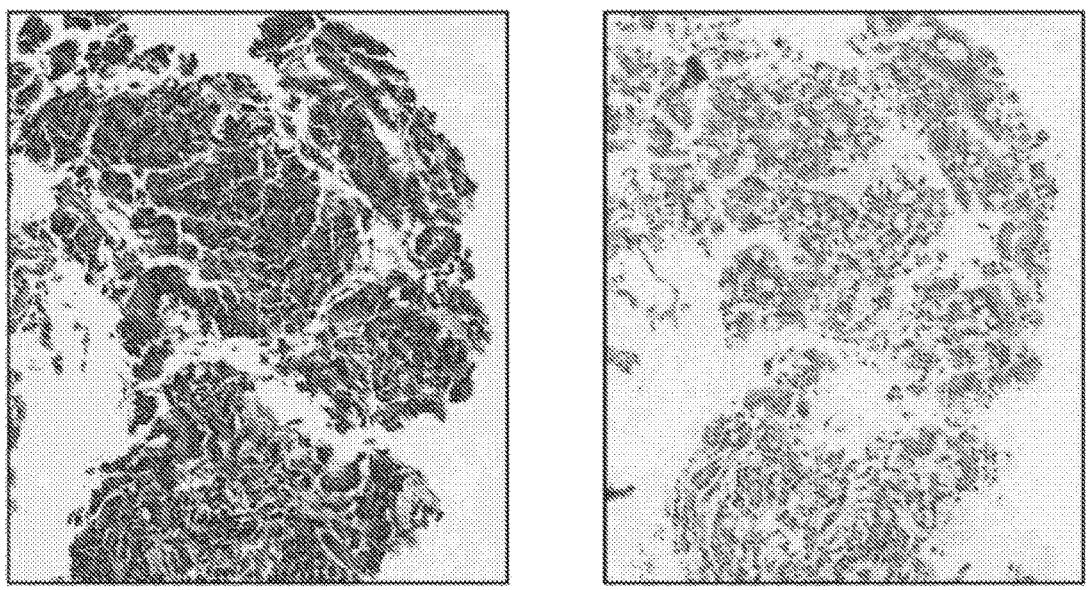
FIG. 2 comprises a table and a set of images illustrating that (top) lung tissue from a prostate cancer patient does not stain for AR; (bottom) bone metastatic lesions are negative in Neuroendocrine (NE) markers (synaptophysin and chromogranin A) regardless of AR status, but lung metastatic lesions are positive for NE markers.

As demonstrated in FIG. 2, lung tissue from a prostate cancer patient did not stain for AR and was positive to NE markers synaptophysin and chromogranin A. However, when AR(−) prostate cancer cells were tested from skeletal lesions, they were found to be negative to NE markers, suggesting that these cells have suppressed AR expression possibly by mechanisms different from the NE transition observed in soft tissue secondary tumors (Table 1).

TABLE 1

| SAMPLE | SYNAPTOPHYSIN | CHROMOGRANIN A |
| --- | --- | --- |
| Mouse Neuronal Culture | Positive | Positive |
| Bone met #1 [AR+] | Negative | Negative |
| Bone met #2 [AR+] | Negative | Negative |
| Bone met #1 [AR−] | Negative | Negative |
| Bone met #2 [AR−] | Negative | Negative |
| Lung [AR−] | Positive | Positive |

Example 3: Role of IL1β in Survival and Proliferation of AR(−) Prostate Cancer Cells The present experiments underline the importance of IL1β in promoting survival and proliferation of AR(−) prostate cancer cells in bone. Anakinra is an antagonist of the receptor for IL1β (IL1R). As demonstrated in FIGS. 3A-3E, in an animal model anakinra significantly impaired the progression at the skeletal level of human prostate cancer cells inoculated in the systemic blood circulation of mice via the left cardiac ventricle.

Figure 3A:
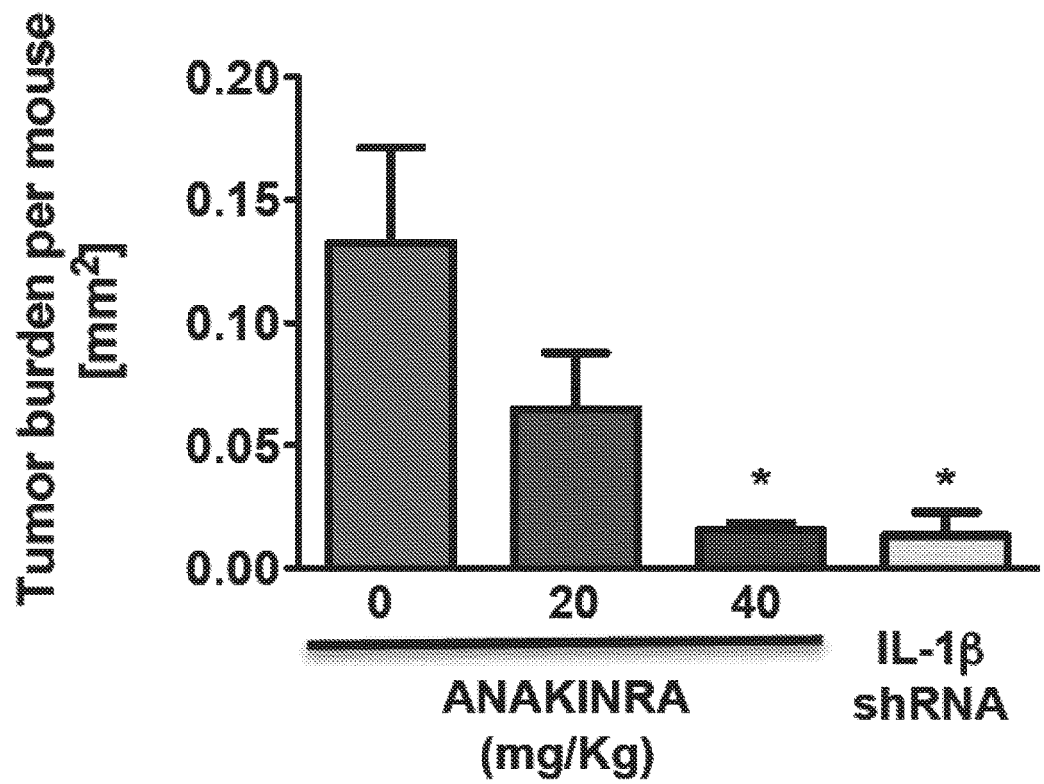
FIG. 3A is a bar graph illustrating tumor burden in the mouse, as a function of treatment regime.
Figure 3B:
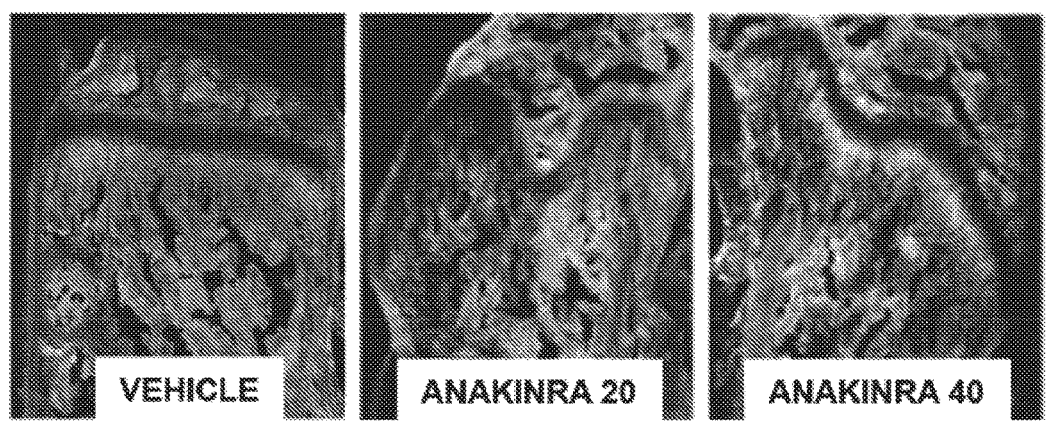
FIG. 3B is a set of images illustrating effects of anakinra treatment in bone metastatic lesions in the mouse.
Figure 3C:
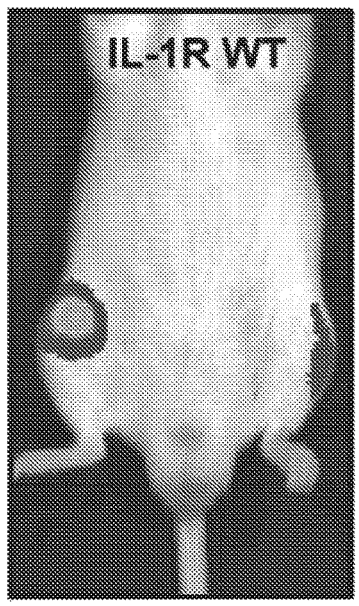
FIGS. 3C-3E illustrate results obtained with a mouse colony of IL1R-knockout SCID mice.
Figure 3C:
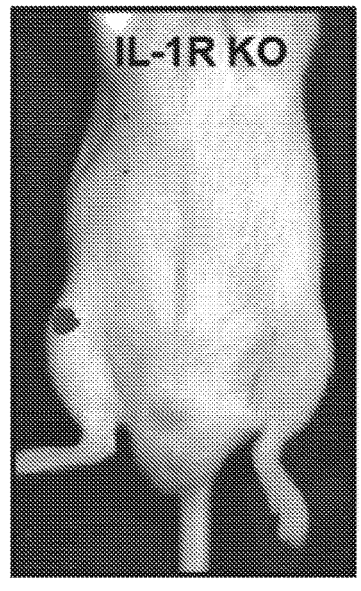
Figure 3C:
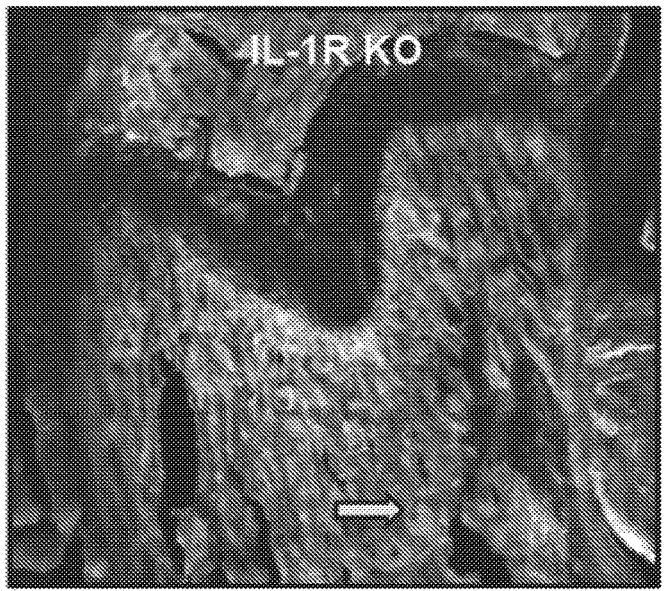
Figure 3D:
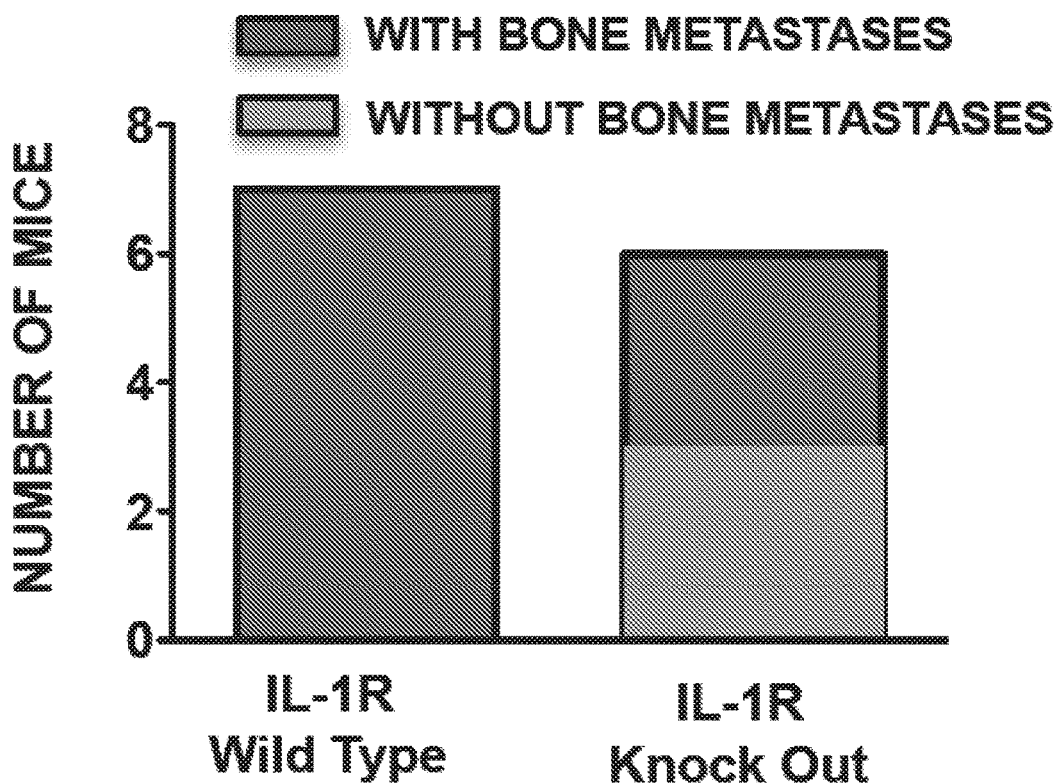
Figure 3E:
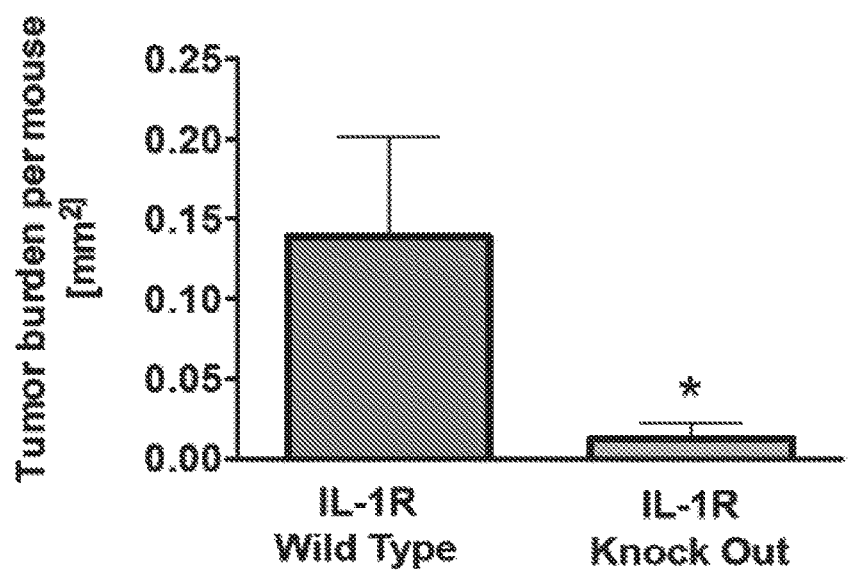

The results obtained with anakinra are similar to those obtained by silencing the expression of IL1β in cancer cells (4th column in FIG. 3A). To ascertain whether anakinra blocks the IL1R located on cancer cells or expressed by stromal cells, a mouse colony of SCID mice also knocked out for IL1R was developed ex novo. As shown in FIGS. 3C-3E, in IL1R knock out animals AR(−)/IL1b(+) prostate cancer cells were dramatically affected in their metastatic progression in the bone. This result indicates that the IL1R on stromal cells is being recruited by the IL1β secreted by cancer cells in the metastatic niche.

Example 4: Bone Stroma

Figure 4A:
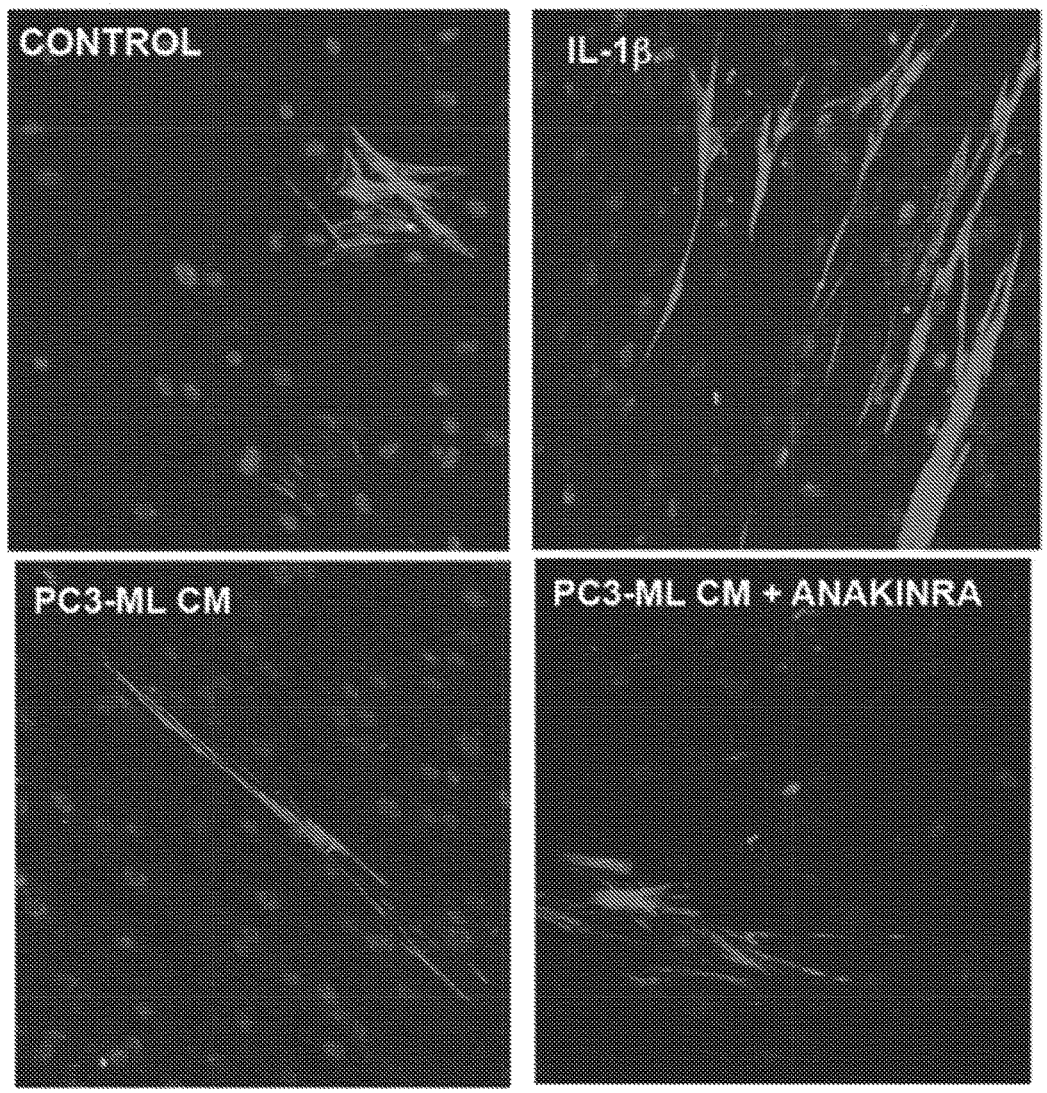
FIG. 4A is a set of images that illustrates morphological changes observed in the alpha smooth muscle actin (alphaMSA) caused by exposing human bone mesenchymal stem cells to IL1β or conditioned medium from AR(−)/IL1β(+) PC3-ML prostate cancer cells.
Figure 4B:
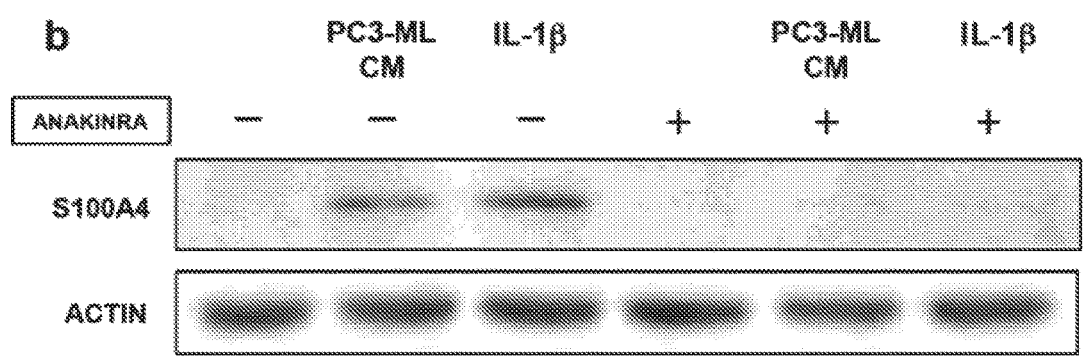
FIG. 4B is set of images illustrating changes in expression of the S100 A4 marker in the system illustrated in FIG. 4A.

These experiments further demonstrate the involvement of bone stroma in the metastatic niche. In vitro studies showed that exposing human bone mesenchymal stem cells to IL1β or conditioned medium from AR(−)/IL1β(+) PC3-ML prostate cancer cells induces a Carcinoma Associated Fibroblasts (CAFs) phenotype, as indicated by the morphological changes observed in the Alpha smooth muscle actin (alpha-MSA)(FIG. 4A) and the expression of the S100 A4 marker (FIG. 4B). Both events were inhibited by anakinra, thus confirming the involvement of IL1β/IL1R interactions.

Figure 4C:
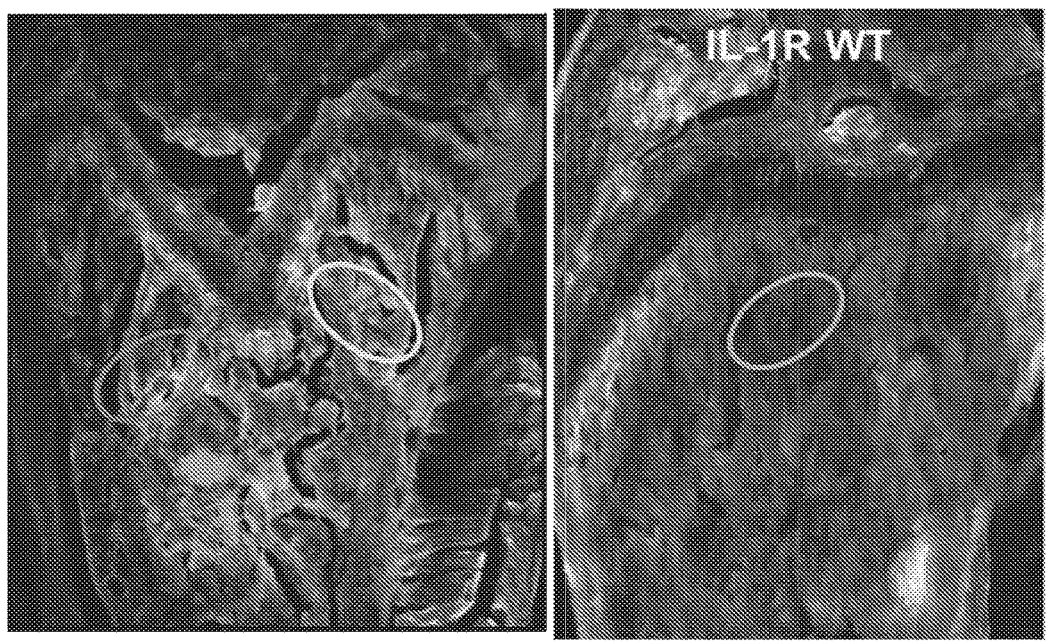
FIGS. 4C-4D are a set of images obtained by harvesting bone stroma in the immediate vicinity of metastatic tumors generated by AR(−)/IL1β (+) cells.
Figure 4D:
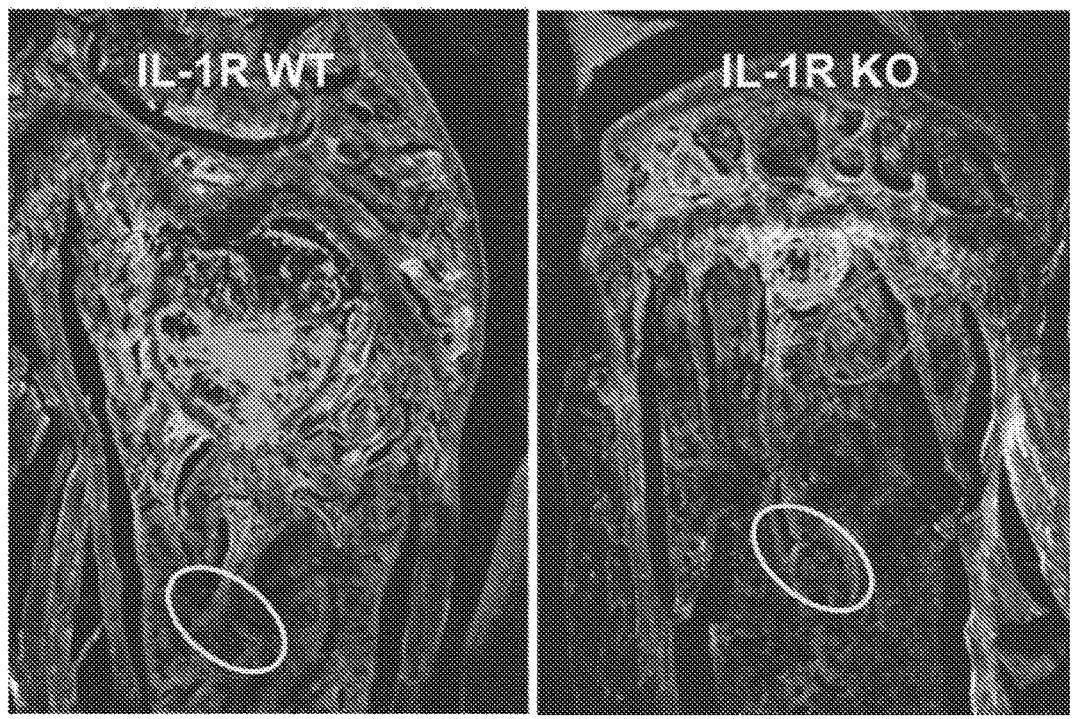
Figure 4E:
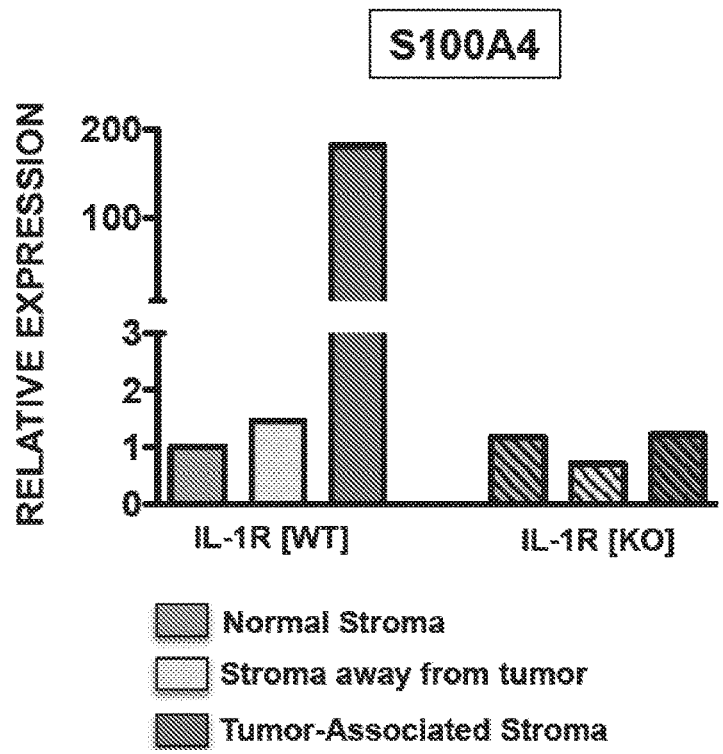
FIGS. 4E-4F are a set of bar graphs illustrating relative expression of S100 A4 (FIG. 4E) and COX-2 (FIG. 4F) in stroma from distinct sources.
Figure 4F:
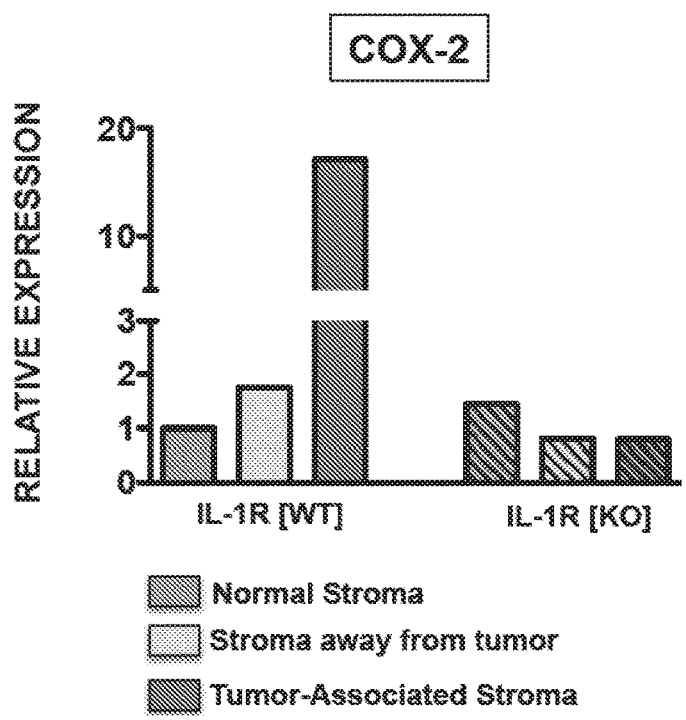

Finally, LCM was used to harvest bone stroma in the immediate vicinity of metastatic tumors generated by AR(−)/IL1β(+) cells and compared the expression of S100 A4 with stroma harvested at some distance from the metastatic tumors or in tumor-free animals (FIG. 4C-4D), mRNA for this marker of CAFs was extremely elevated only in the stroma close to the tumors (FIG. 4E), indicating that CAFs are induced by IL1β secreted by cancer cells and activating IL1R in the tumor surrounding. These results are consistent with the in vitro experiments reported elsewhere herein. Since IL1β is able to induce the expression of the enzyme Cyclo-oxygenase 2 (COX-2) in stromal cells, the bone stroma collected from the locations described above was tested high levels of COX-2 induced by the cancer cells were found (FIG. 4F).

Example 5: Further Characterization of AR(−) and AR(+) Prostate Cancer Cells

Figure 5A:
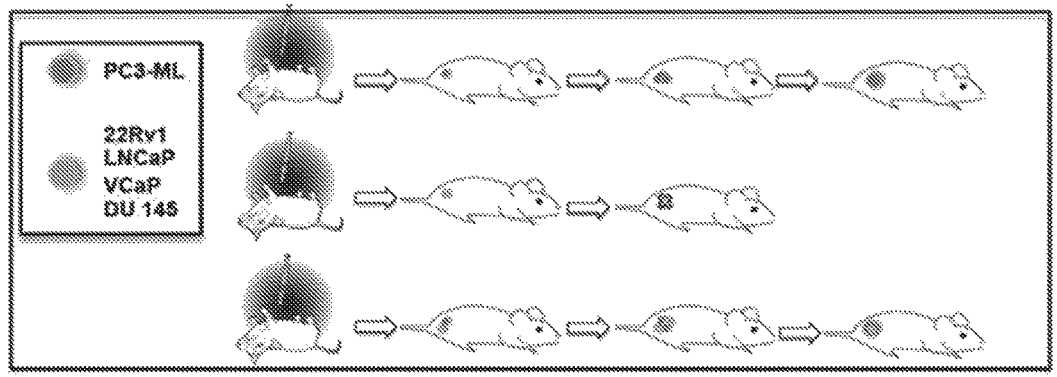
FIG. 5A is a schematic illustration of experiments wherein mice were co-inoculated with AR(−)/IL1β(+) prostate cancer cells stably expressing red bioluminescent/fluorescent markers, and AR(+)/IL1β(−) cancer cells stably expressing green bioluminescent/fluorescent markers.
Figure 5B:
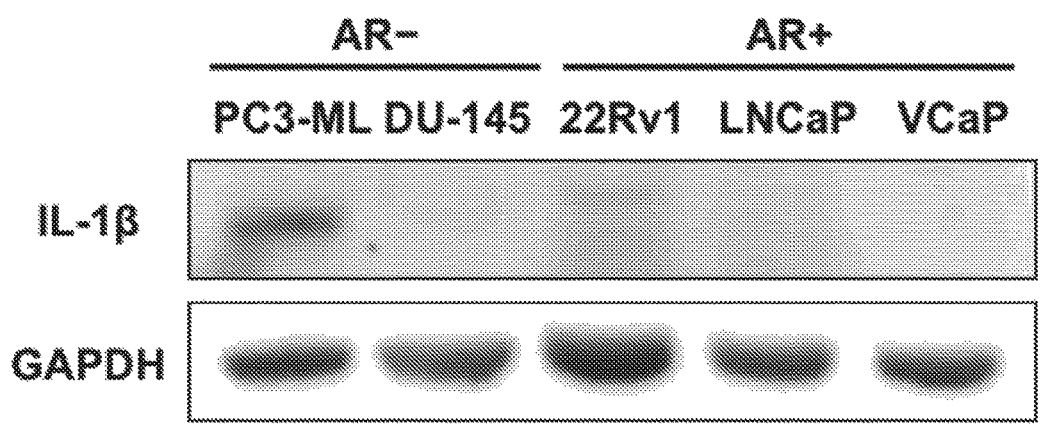
FIG. 5B is an image depicting a Western blot demonstrating a lack of IL-1 expression in human PCa cells lacking DU-145 or expressing LNCAP, VCaP or 22RV1.
Figure 5C:
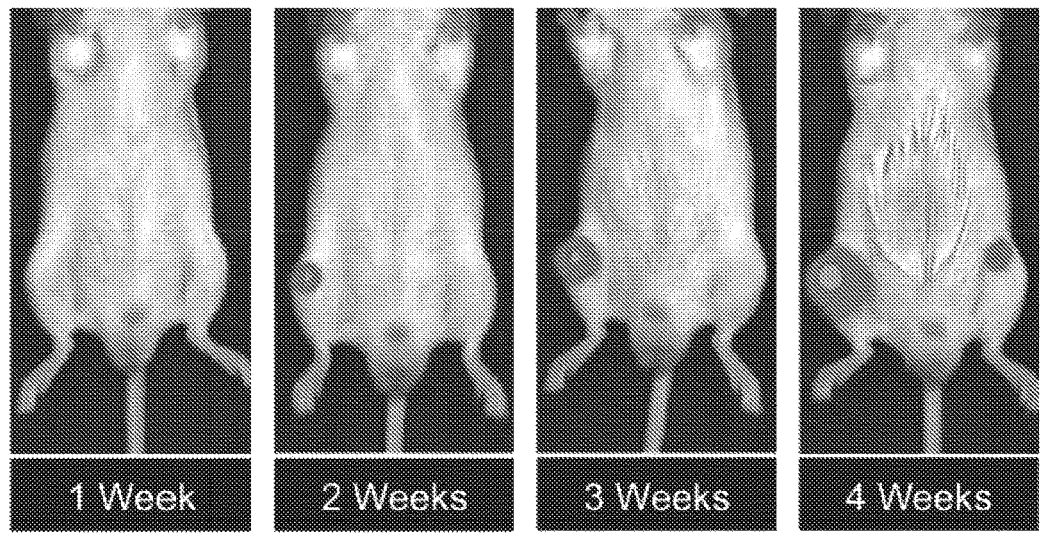
FIGS. 5C-5H are a set of bar graphs and images illustrating bone metastatic lesions observed with the experimental setup of FIG. 5A. AR(+) cells were able to survive and colonize the bone when coexisting with AR(−)/IL1β(+) cells. DU-145 cells (which are AR(−)/IL1β(−)) also benefited from the presence of AR(−)/IL1β(+) cancer cells, although they generated smaller tumors (FIG. 5H).
Figure 5D:
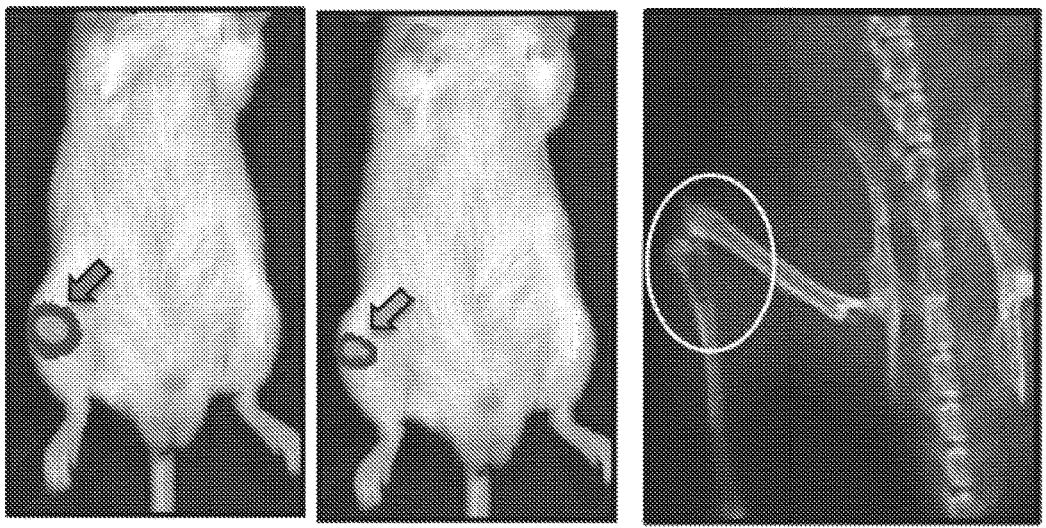
Figure 5E:
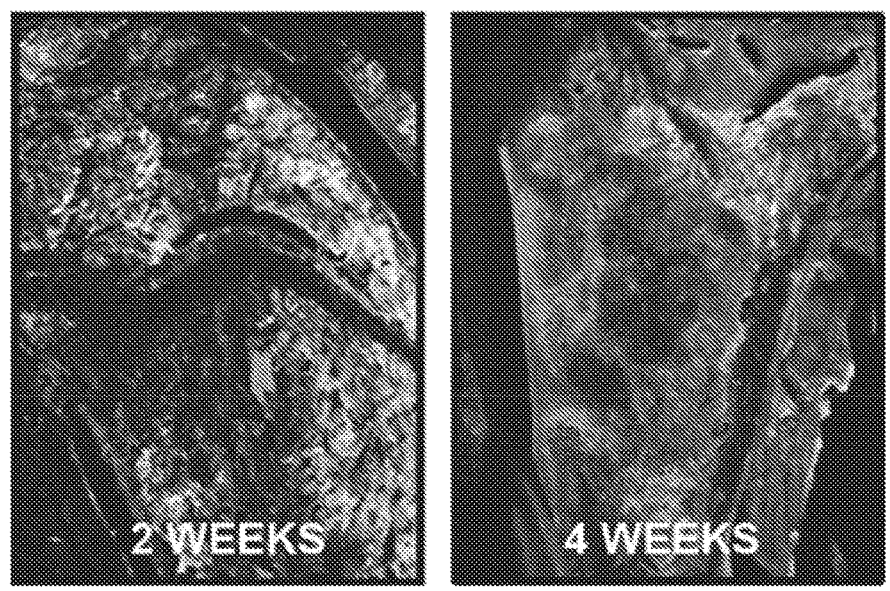
Figure 5F:
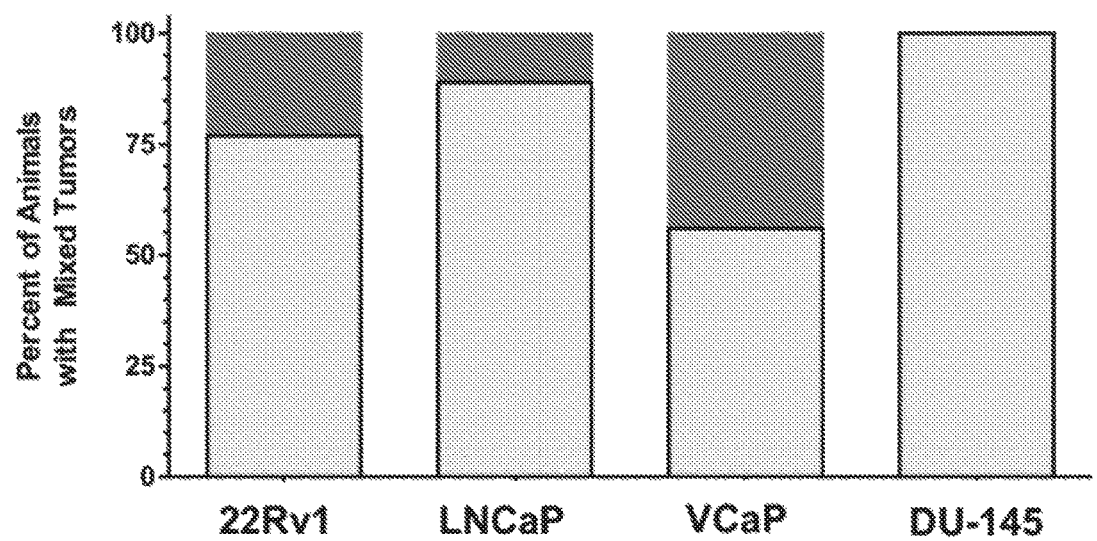
Figure 5G:
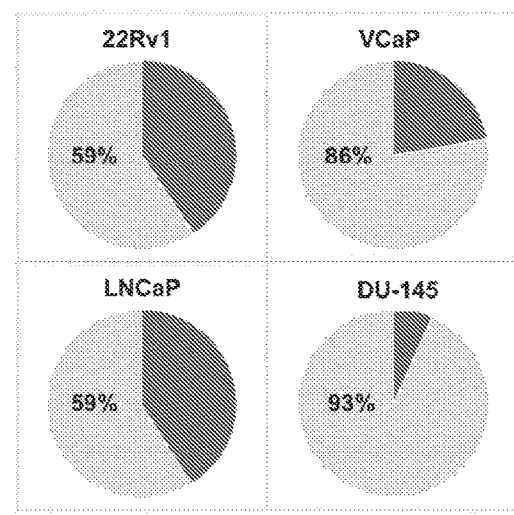
Figure 5H:
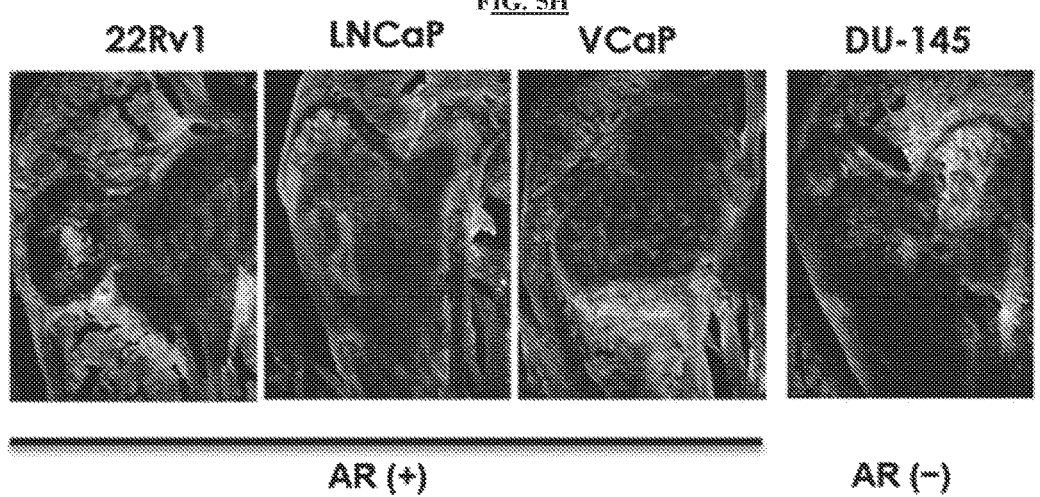
Figure 5I:
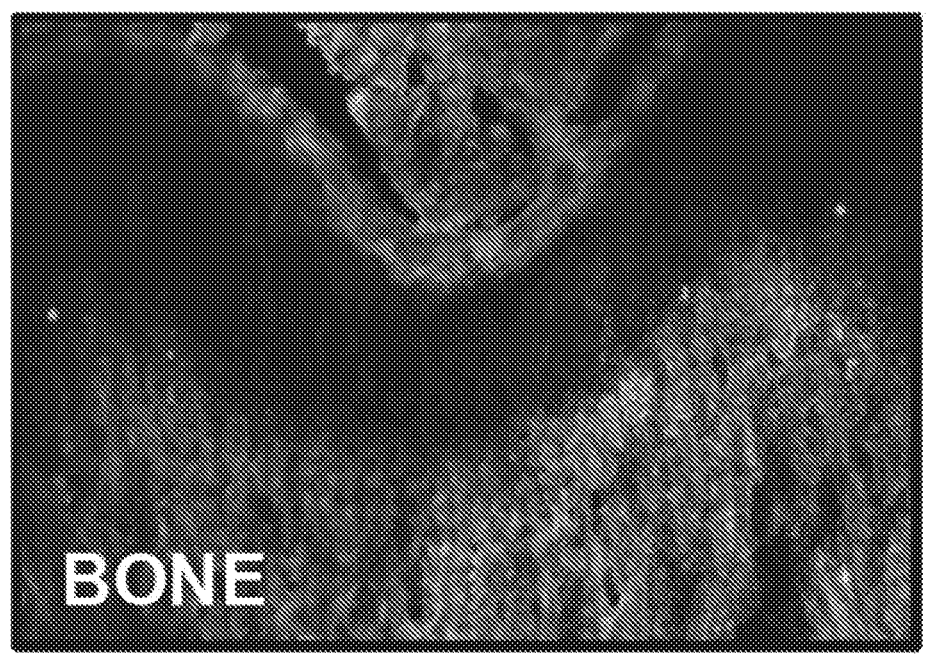
FIGS. 5I-5K are a set of bar graphs and images illustrating the number of disseminated tumor cells (DTCs) in the bone (FIG. 5I) detected at 24 hours post-inoculation (FIG. 5J) and 5 minutes post-inoculation (FIG. 5K), as observed with the experimental setup of FIG. 5A.

Since IL1β secreted by AR(−) prostate cancer cells is responsible for supporting their survival and colonization in the bone, it was further investigated whether IL1β supports prostate cancer cells that are unable to metastasize independently in the present animal model. AR(+) human prostate cancer cells (22Rv1, LNCaP, VCaP) lack IL1β expression and fail to survive in the bone microenvironment after disseminating through the systemic blood circulation (FIG. 5B). In these studies, AR(−)/IL1β(+) prostate cancer cells stably expressing red bioluminescent and fluorescent markers were co-inoculated with one type of AR(+)/IL1β(−) cancer cells that were stably expressing green bioluminescent and fluorescent markers (FIG. 5A). AR(+) cells were found to be able to survive and colonize the bone when coexisting with AR(−)/IL1β(+) cells (FIGS. 5C-5H). The majority of animals in each study were found to harbor mixed tumors at 4 weeks, as indicated by BLI (FIG. 5F), while overall fraction of AR-mixed tumors promoted by PC3-ML cells varied from 59% for LNCaP and 22Rv1 cells to 86% for VCaP (FIG. 5G). DU-145 cells, which are AR(−) and also IL1β(−), also benefited from the presence of AR(−)/IL1β(+) cancer cells, although they generated tumors of smaller size (FIG. 5H).

Taken together, these results indicate that AR(−) cells show a metastatic behavior similar to AR(+) cells that lack IL1β expression, further emphasizing the role of this cytokine in promoting the metastatic potential of prostate cancer cells.

Figure 5J:
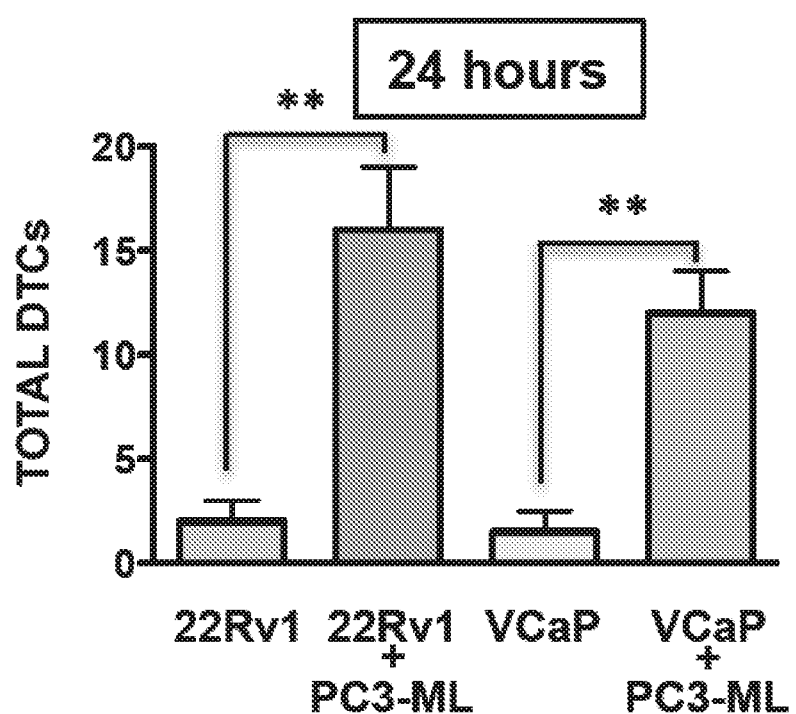
Figure 5K:
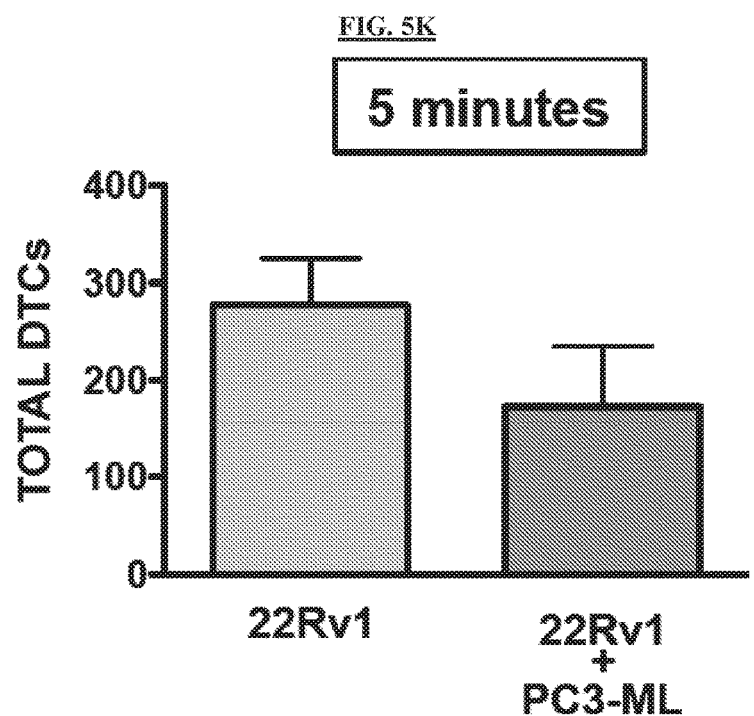
Figure 5L:
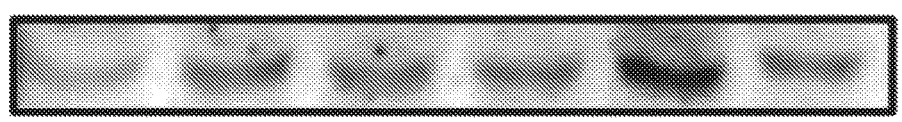
FIGS. 5L-5N are a set of images of Western blots meant to investigate the trajectory of IL-1 signaling.
Figure 5L:
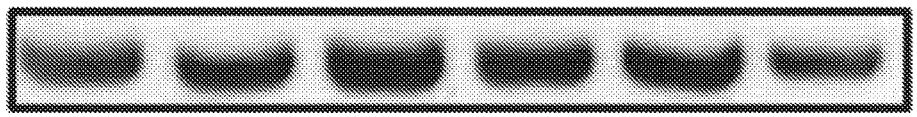
Figure 5M:
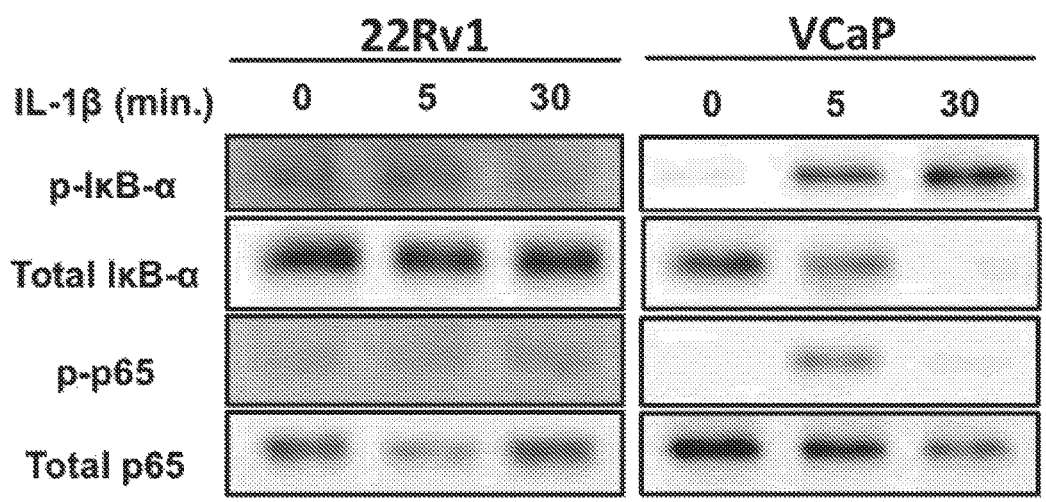
Figure 5N:
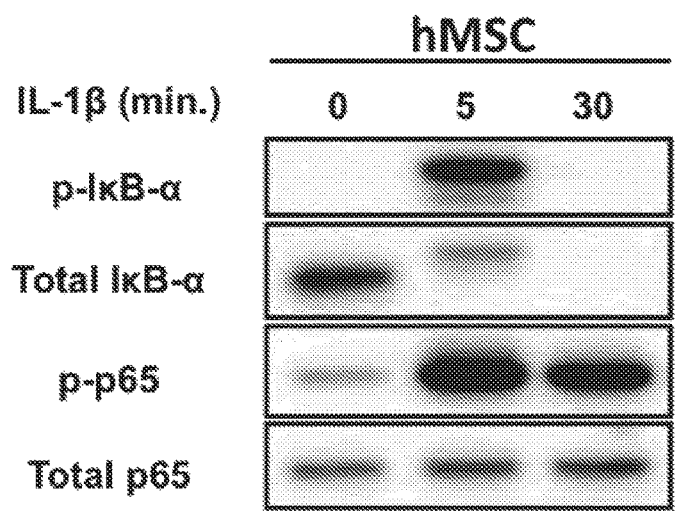
Figure 5O:
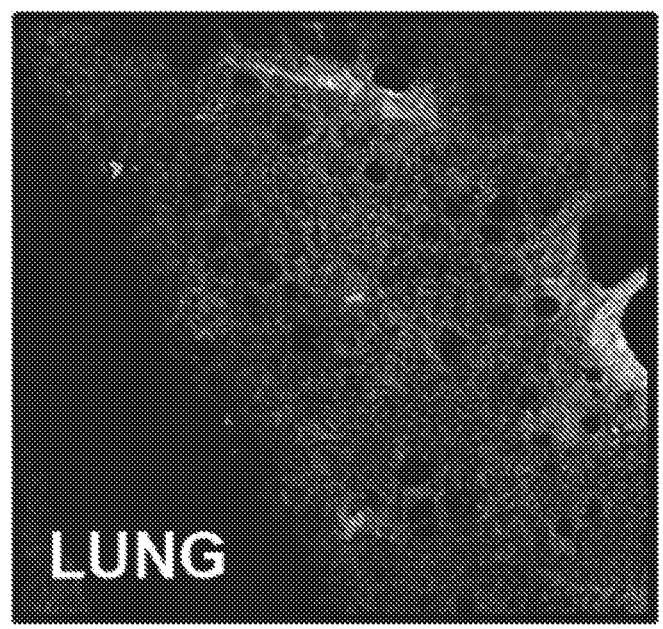
FIGS. 5O-5P are a set of bar graphs and images illustrating the number of disseminated tumor cells (DTCs, FIG. 5O) in the lung (FIG. 5P) post-inoculation, as observed with the experimental setup of FIG. 5A.
Figure 5P:
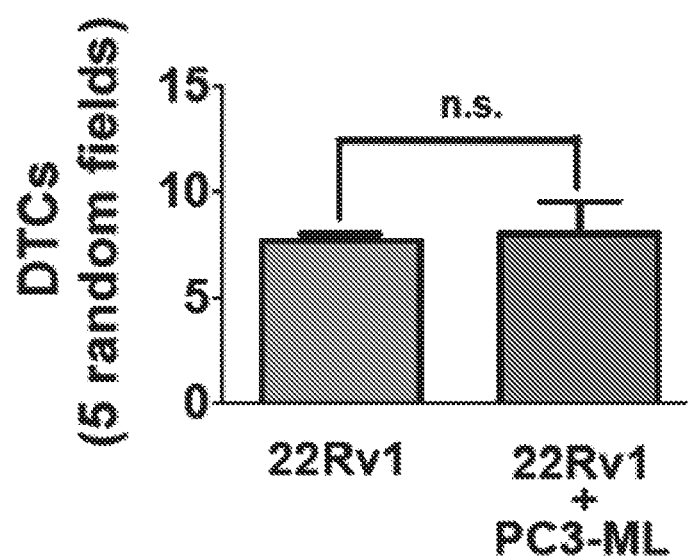

Furthermore, the present studies reveal a novel form of cancer-cell cooperation that relies on IL1β-mediated recruitment of bone stroma in the metastatic niche. Additional experiments show that this cooperation is not necessary for the initial arrival of cancer cells to the skeleton—measured as number of disseminated tumor cells (DTCs) detected at 5 minutes post-inoculation (FIG. 5K), but supports the survival of DTCs following their arrival (FIG. 5J). Further, the IL-1β mediated support of AR(+) cancer cells appears to be specific for the bone tissue, since the number of AR(+) 22Rv1 cells homing to the lung was similar with or without simultaneous presence of AR(−)/IL1β(+) PC3-ML cells (FIGS. 5O-5P). This was determined by assaying various PCa cell lines used in this study for expression of the IL-1R in order to determine their potential receptivity to paracrine IL-1β signaling, and the receptor was found to be present in each (FIG. 5L). However, exposure to IL-1β peptide in vitro revealed a varying profile of signal transduction among two AR+ PCa cell lines that benefited equally from PC3-ML cells when colonizing the bone, suggesting that paracrine stimulation of IL-1R is unlikely to be primarily responsible for the metastatic cell cooperation that was observed (FIG. 5M). On the other hand, human bone Mesenchymal Stem Cells (hMSCs), which are an abundant component of the bone stroma, when similarly exposed to IL-1β exhibited a rapid and sustained signaling response, indicating definite susceptibility to this cytokine (FIG. 5N).

Figure 5Q:
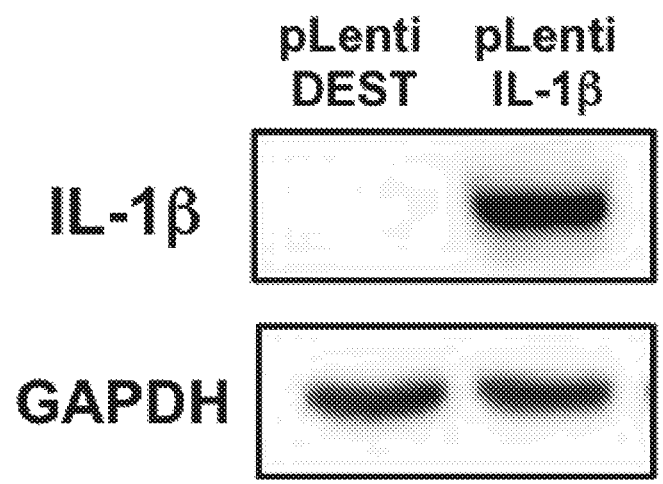
FIGS. 5Q-5S are a set of bar graphs and images illustrating the results of administering non-metastatic and AR-DU-145 cell lines, expressing high levels of IL-D, to a mouse.
Figure 5R:
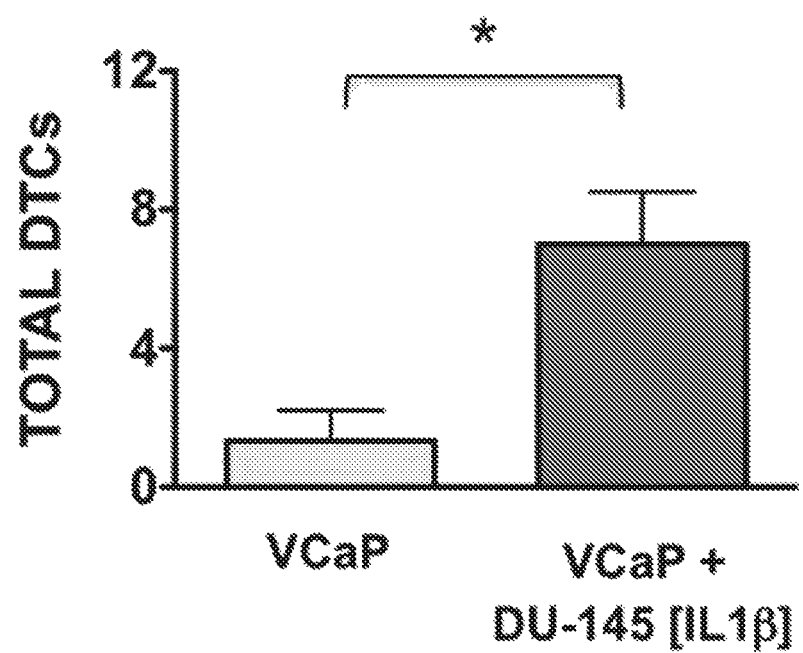
Figure 5S:
Figure 6:
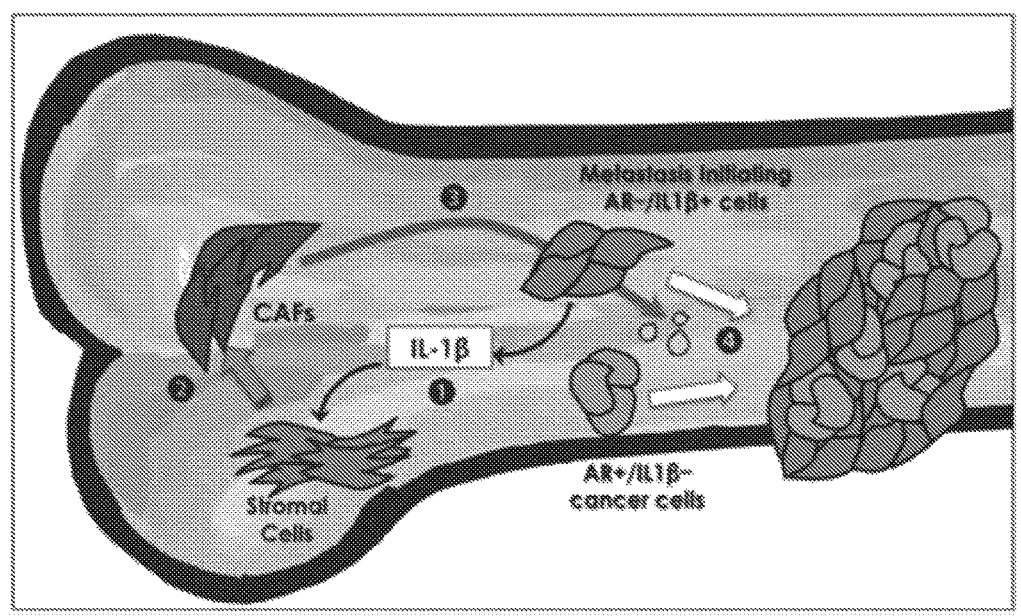
FIG. 6 depicts a diagram of a novel model of bone metastatic niche in which prostate cancer cells lacking the androgen receptor exert a Metastasis-Initiating role by secreting IL-1β.

These findings were further supported by using non-metastatic and AR-DU-145 cell lines engineered to stably express high levels of IL-1β (FIG. 5Q), which has shown to impart them with de novo metastatic ability. These cells were labeled with mCherry and co-injected with GFP-labeled VCap cells and the mice were sacrificed after either 24 hours or three weeks. Upon examination of their femora and tibiae, a significant increase in both arrival and seeding of VCaP cells was observed (FIG. 5R) as was the generation of mixed tumors (FIG. 5S) relative to their solitary inoculation. This indicates that both PC3-ML cells and DU-145 cells exogenously expressing IL-1β, thus modeling the AR− prostate phenotypes that populate the skeletal metastases in the advanced PCa patients examined, promote the early bone colonization by independently non-metastatic AR+ cells.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of killing, or reducing the growth rate of, a prostate cancer cell that does not express androgen receptor [AR(−) PC cell], wherein the cancer cell is part of a solid tumor within a human subject, the method comprising contacting the AR(−) PC cell with a composition consisting essentially of an effective amount of an IL1β-depleting agent selected from the group consisting of anakinra, XOMA-052, AMG-108, canakinumab, rilonacept, K-832, CYT-013-IL1bQb, LY-2189102, dexamethasone, interferon-gamma, pentoxifylline, and any combinations thereof, whereby the cell is killed or growth rate of the cell is reduced.

2. The method of claim 1, wherein the solid tumor comprises a prostate tumor or a bone metastasis.

3. A method of treating or reducing rate of metastasis of a AR(−) PC cell in a human subject, the method comprising administering to the subject a composition consisting essentially of a therapeutically effective amount of an IL1 β-depleting agent selected from the group consisting of anakinra, XOMA-052, AMG-108, canakinumab, rilonacept, K-832, CYT-013-IL1bQb, LY-2189102, dexamethasone, interferon-gamma, pentoxifylline, and any combinations thereof, whereby metastasis of the AR(−) PC cell in the subject is treated or metastasis rate of the AR(−) PC cell in the subject is reduced.

4. The method of claim 3, wherein the metastasis comprises bone metastasis.

5. The method of claim 3, wherein the subject suffers from castration-resistant prostate cancer.

6. The method of claim 3, wherein the IL1β-depleting agent is administered to the subject by an administration route selected from the group consisting of inhalational, oral, rectal, vaginal, parenteral, topical, transdermal, pulmonary, intranasal, buccal, ophthalmic, intrathecal, and any combinations thereof.

* * * * *

SEQUENCE LISTING

<160> NUMBER OF SEQ ID NOS: 9

<210> SEQ ID NO 1
<211> LENGTH: 269

```
<212> TYPE: PRT
<213> ORGANISM: Homo sapiens

<400> SEQUENCE: 1

Met Ala Glu Val Pro Glu Leu Ala Ser Glu Met Ala Tyr Tyr Ser
1               5                   10                  15

Gly Asn Glu Asp Asp Leu Phe Phe Glu Ala Asp Gly Pro Lys Gln Met
                20                  25                  30

Lys Cys Ser Phe Gln Asp Leu Asp Leu Cys Pro Leu Asp Gly Gly Ile
                35                  40                  45

Gln Leu Arg Ile Ser Asp His His Tyr Ser Lys Gly Phe Arg Gln Ala
        50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                    85                  90                  95

Ile Phe Glu Glu Glu Pro Ile Phe Phe Asp Thr Trp Asp Asn Glu Ala
                100                 105                 110

Tyr Val His Asp Ala Pro Val Arg Ser Leu Asn Cys Thr Leu Arg Asp
            115                 120                 125

Ser Gln Gln Lys Ser Leu Val Met Ser Gly Pro Tyr Glu Leu Lys Ala
130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
                180                 185                 190

Lys Pro Thr Leu Gln Leu Glu Ser Val Asp Pro Lys Asn Tyr Pro Lys
            195                 200                 205

Lys Lys Met Glu Lys Arg Phe Val Phe Asn Lys Ile Glu Ile Asn Asn
        210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
            260                 265

<210> SEQ ID NO 2
<211> LENGTH: 153
<212> TYPE: PRT
<213> ORGANISM: Homo sapiens

<400> SEQUENCE: 2

Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
                20                  25                  30

Gly Gln Asp Met Glu Gln Gln Val Val Phe Ser Met Ser Phe Val Gln
                35                  40                  45

Gly Glu Glu Ser Asn Asp Lys Ile Pro Val Ala Leu Gly Leu Lys Glu
            50                  55                  60

Lys Asn Leu Tyr Leu Ser Cys Val Leu Lys Asp Asp Lys Pro Thr Leu
65                  70                  75                  80
```

Gln Leu Glu Ser Val Asp Pro Lys Asn Tyr Pro Lys Lys Met Glu
            85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
            115                 120                 125

Asn Met Pro Val Phe Leu Gly Gly Thr Lys Gly Gly Gln Asp Ile Thr
        130                 135                 140

Asp Phe Thr Met Gln Phe Val Ser Ser
145                 150

<210> SEQ ID NO 3
<211> LENGTH: 272
<212> TYPE: PRT
<213> ORGANISM: Homo sapiens

<400> SEQUENCE: 3

Met Gly Asn Arg Gly Gly Phe Arg Gly Gly Phe Gly Ser Gly Ile Arg
1               5                   10                  15

Gly Arg Gly Arg Gly Arg Gly Arg Gly Arg Gly Arg Gly Arg Gly Ala
            20                  25                  30

Arg Gly Gly Lys Ala Glu Asp Lys Glu Trp Met Pro Val Thr Lys Leu
        35                  40                  45

Gly Arg Leu Val Lys Asp Met Lys Ile Lys Ser Leu Glu Glu Ile Thr
    50                  55                  60

Leu Phe Ser Leu Pro Ile Lys Glu Ser Glu Ile Ile Asp Phe Phe Leu
65                  70                  75                  80

Gly Ala Ser Leu Lys Asp Glu Val Leu Lys Ile Met Pro Val Gln Lys
                85                  90                  95

Gln Thr Arg Ala Gly Gln Arg Thr Arg Phe Lys Ala Phe Val Ala Ile
            100                 105                 110

Gly Asp Tyr Asn Gly His Val Gly Leu Gly Val Lys Cys Ser Lys Glu
        115                 120                 125

Val Ala Thr Ala Ile Arg Gly Ala Ile Ile Leu Ala Lys Leu Ser Ile
    130                 135                 140

Val Pro Val Arg Arg Gly Tyr Trp Gly Asn Asn Ile Gly Lys Ala His
145                 150                 155                 160

Thr Val Arg Cys Lys Val Thr Gly Arg Cys Gly Ser Val Leu Val Arg
                165                 170                 175

Leu Ile Pro Ala Pro Arg Gly Thr Gly Ile Val Ser Ala Pro Val Pro
            180                 185                 190

Lys Lys Leu Leu Met Met Ala Gly Ile Asp Asp Cys Tyr Thr Ser Ala
        195                 200                 205

Arg Gly Cys Thr Ala Thr Leu Gly Asn Phe Ala Lys Ala Thr Phe Asp
    210                 215                 220

Ala Ile Ser Lys Thr Tyr Ser Tyr Leu Thr Pro Asp Leu Trp Lys Glu
225                 230                 235                 240

Thr Val Phe Thr Lys Ser Pro Tyr Gln Glu Phe Thr Asp His Leu Val
                245                 250                 255

Lys Thr His Thr Arg Val Ser Val Gln Arg Thr Gln Ala Pro Ala Val
            260                 265                 270

<210> SEQ ID NO 4
<211> LENGTH: 20
<212> TYPE: DNA
<213> ORGANISM: Artificial Sequence

```
<220> FEATURE:
<223> OTHER INFORMATION: PCR primer

<400> SEQUENCE: 4
ggaaaagaat tggtatccac                                              20

<210> SEQ ID NO 5
<211> LENGTH: 21
<212> TYPE: DNA
<213> ORGANISM: Artificial Sequence
<220> FEATURE:
<223> OTHER INFORMATION: PCR primer

<400> SEQUENCE: 5
agttataaca gctgggttgg c                                            21

<210> SEQ ID NO 6
<211> LENGTH: 29
<212> TYPE: DNA
<213> ORGANISM: Artificial Sequence
<220> FEATURE:
<223> OTHER INFORMATION: PCR primer

<400> SEQUENCE: 6
ccacatattc tccatcatct ctgctggta                                    29

<210> SEQ ID NO 7
<211> LENGTH: 29
<212> TYPE: DNA
<213> ORGANISM: Artificial Sequence
<220> FEATURE:
<223> OTHER INFORMATION: PCR primer

<400> SEQUENCE: 7
tttcgaatct cagttgtcaa gtgtgtccc                                    29

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
ctgaatgaac tgcaggacga                                              20

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
atactttctc ggcaggagca                                              20
```